United States Patent
Park et al.

(10) Patent No.: US 9,600,994 B2
(45) Date of Patent: Mar. 21, 2017

(54) PORTABLE MONITORING DEVICES AND METHODS OF OPERATING THE SAME

(71) Applicant: Fitbit, Inc., San Francisco, CA (US)

(72) Inventors: James Park, Berkeley, CA (US); Shelten Gee Jao Yuen, Berkeley, CA (US); Eric Nathan Friedman, San Francisco, CA (US); Christine Boomer Brumback, San Francisco, CA (US)

(73) Assignee: Fitbit, Inc., San Francisco, CA (US)

( * ) Notice: Subject to any disclaimer, the term of this patent is extended or adjusted under 35 U.S.C. 154(b) by 0 days.

(21) Appl. No.: 15/017,356

(22) Filed: Feb. 5, 2016

(65) Prior Publication Data
US 2016/0267764 A1    Sep. 15, 2016

Related U.S. Application Data

(63) Continuation of application No. 14/524,909, filed on Oct. 27, 2014, now Pat. No. 9,286,789, which is a
(Continued)

(51) Int. Cl.
*G06F 19/00* (2011.01)
*G08B 21/04* (2006.01)
(Continued)

(52) U.S. Cl.
CPC ........ *G08B 21/0446* (2013.01); *A61B 5/0002* (2013.01); *A61B 5/01* (2013.01);
(Continued)

(58) Field of Classification Search
CPC ............ G06Q 30/02; G02B 2027/0178; G02B 27/017
(Continued)

(56) References Cited

U.S. PATENT DOCUMENTS

| | | |
|---|---|---|
| 4,938,228 A | 7/1990 | Righter et al. |
| 5,339,294 A | 8/1994 | Rodgers |

(Continued)

FOREIGN PATENT DOCUMENTS

| | | |
|---|---|---|
| CN | 101785675 A | 7/2010 |
| CN | 102930490 A | 2/2013 |

(Continued)

OTHER PUBLICATIONS

US Office Action, dated Feb. 12, 2015, issued in U.S. Appl. No. 14/029,763.

(Continued)

*Primary Examiner* — Edward Raymond
(74) *Attorney, Agent, or Firm* — Weaver Austin Villeneuve & Sampson LLP

(57) ABSTRACT

In one aspect of the disclosed implementations, a device includes one or more motion sensors for sensing motion of the device and providing activity data indicative of the sensed motion. The device also includes one or more processors for monitoring the activity data, and receiving or generating annotation data for annotating the activity data with one or more markers or indicators to define one or more characteristics of an activity session. The device also includes one or more feedback devices for providing feedback, a notice, or an indication to a user based on the monitoring. The device further includes a portable housing that encloses at least portions of the motion sensors, the processors and the feedback devices.

30 Claims, 3 Drawing Sheets

Related U.S. Application Data continuation of application No. 14/062,717, filed on Oct. 24, 2013, now Pat. No. 8,903,671, which is a continuation of application No. 14/029,759, filed on Sep. 17, 2013, now abandoned.

(60) Provisional application No. 61/830,600, filed on Jun. 3, 2013, provisional application No. 61/752,826, filed on Jan. 15, 2013.

(51) Int. Cl.

| | | |
|---|---|---|
| G08C 17/02 | (2006.01) | |
| A61B 5/00 | (2006.01) | |
| G08B 21/02 | (2006.01) | |
| A61B 5/11 | (2006.01) | |
| G08B 21/18 | (2006.01) | |
| G06F 17/30 | (2006.01) | |
| G08B 5/22 | (2006.01) | |
| G08B 6/00 | (2006.01) | |
| G08B 25/10 | (2006.01) | |
| A61B 5/01 | (2006.01) | |
| A61B 5/021 | (2006.01) | |
| A61B 5/024 | (2006.01) | |
| A61B 5/0205 | (2006.01) | |

(52) U.S. Cl.
CPC ............ *A61B 5/021* (2013.01); *A61B 5/024* (2013.01); *A61B 5/1118* (2013.01); *A61B 5/681* (2013.01); *G06F 17/30312* (2013.01); *G08B 5/22* (2013.01); *G08B 6/00* (2013.01); *G08B 21/02* (2013.01); *G08B 21/18* (2013.01); *G08B 25/10* (2013.01); *G08C 17/02* (2013.01); *A61B 5/0022* (2013.01); *A61B 5/02055* (2013.01)

(58) Field of Classification Search
USPC .................. 702/104, 150, 182–185, 188
See application file for complete search history.

(56) References Cited

U.S. PATENT DOCUMENTS

| | | | |
|---|---|---|---|
| 5,612,931 | A | 3/1997 | Sato et al. |
| 5,876,350 | A | 3/1999 | Lo et al. |
| 5,946,274 | A | 8/1999 | Yamaguchi et al. |
| 5,978,923 | A | 11/1999 | Kou |
| 6,300,947 | B1 | 10/2001 | Kanevsky |
| 6,469,718 | B1 | 10/2002 | Setogawa et al. |
| 6,583,369 | B2 | 6/2003 | Montagnino et al. |
| 6,888,927 | B1 | 5/2005 | Cruickshank et al. |
| 7,155,729 | B1 | 12/2006 | Andrew et al. |
| 7,254,516 | B2 | 8/2007 | Case, Jr. et al. |
| 7,334,472 | B2 | 2/2008 | Seo et al. |
| 7,458,014 | B1 | 11/2008 | Rubin et al. |
| 7,559,877 | B2 | 7/2009 | Parks et al. |
| 7,662,065 | B1 | 2/2010 | Kahn et al. |
| 7,717,866 | B2 | 5/2010 | Damen |
| 7,793,361 | B2 | 9/2010 | Ishihara et al. |
| 7,913,185 | B1 | 3/2011 | Benson et al. |
| 8,162,804 | B2 | 4/2012 | Tagliabue |
| 8,172,761 | B1 | 5/2012 | Rulkov et al. |
| 8,180,591 | B2 | 5/2012 | Yuen et al. |
| 8,306,508 | B1 | 11/2012 | Lundy et al. |
| 8,365,073 | B2 | 1/2013 | Kim et al. |
| 8,441,356 | B1 | 5/2013 | Tedesco et al. |
| 8,600,457 | B2 | 12/2013 | Vargas et al. |
| 8,630,741 | B1 * | 1/2014 | Matsuoka ........... H04L 12/2829 700/12 |
| 8,734,296 | B1 | 5/2014 | Brumback et al. |
| 8,784,271 | B2 | 7/2014 | Brumback et al. |
| 8,896,526 | B1 | 11/2014 | Park |
| 8,903,671 | B2 | 12/2014 | Park et al. |
| 8,944,958 | B1 | 2/2015 | Brumback et al. |
| 8,947,239 | B1 | 2/2015 | Park |
| 9,017,221 | B2 | 4/2015 | Brumback et al. |
| 9,026,927 | B2 | 5/2015 | Brumback et al. |
| 9,050,488 | B2 | 6/2015 | Brumback et al. |
| 9,098,991 | B2 | 8/2015 | Park et al. |
| 9,286,789 | B2 | 3/2016 | Park et al. |
| 2001/0002122 | A1 | 5/2001 | Vong et al. |
| 2002/0161644 | A1 | 10/2002 | Duffield |
| 2004/0059790 | A1 | 3/2004 | Austin-Lane et al. |
| 2004/0127198 | A1 | 7/2004 | Roskind et al. |
| 2004/0152957 | A1 | 8/2004 | Stivoric et al. |
| 2005/0115561 | A1 * | 6/2005 | Stahmann ............ A61B 5/0031 128/200.24 |
| 2005/0245793 | A1 | 11/2005 | Hilton et al. |
| 2005/0250551 | A1 | 11/2005 | Helle |
| 2006/0020177 | A1 | 1/2006 | Seo et al. |
| 2006/0028429 | A1 | 2/2006 | Kanevsky et al. |
| 2006/0036642 | A1 | 2/2006 | Horvitz et al. |
| 2006/0090139 | A1 | 4/2006 | Jenni et al. |
| 2006/0242590 | A1 | 10/2006 | Polivy et al. |
| 2006/0259537 | A1 | 11/2006 | Emberton et al. |
| 2006/0277100 | A1 | 12/2006 | Parham |
| 2006/0293041 | A1 | 12/2006 | Kim |
| 2007/0049836 | A1 | 3/2007 | Chen |
| 2007/0118043 | A1 | 5/2007 | Oliver et al. |
| 2007/0143068 | A1 | 6/2007 | Pasolini et al. |
| 2007/0173327 | A1 | 7/2007 | Kilgore et al. |
| 2007/0188468 | A1 | 8/2007 | Lee et al. |
| 2007/0219059 | A1 | 9/2007 | Schwartz et al. |
| 2007/0293371 | A1 | 12/2007 | Hilfiker et al. |
| 2008/0070603 | A1 | 3/2008 | Mao |
| 2008/0155455 | A1 | 6/2008 | Balasubramanian |
| 2008/0157956 | A1 | 7/2008 | Radivojevic et al. |
| 2008/0191885 | A1 | 8/2008 | Loree, IV et al. |
| 2008/0200312 | A1 | 8/2008 | Tagliabue |
| 2008/0243432 | A1 | 10/2008 | Kato et al. |
| 2008/0249736 | A1 | 10/2008 | Prstojevich |
| 2008/0269625 | A1 | 10/2008 | Halperin et al. |
| 2008/0301250 | A1 | 12/2008 | Hardy et al. |
| 2008/0319330 | A1 | 12/2008 | Juntunen et al. |
| 2009/0043531 | A1 | 2/2009 | Kahn et al. |
| 2009/0105047 | A1 | 4/2009 | Guidi et al. |
| 2009/0125917 | A1 | 5/2009 | Parker et al. |
| 2009/0167542 | A1 | 7/2009 | Culbert et al. |
| 2009/0192391 | A1 | 7/2009 | Lovitt et al. |
| 2009/0195497 | A1 | 8/2009 | Fitzgerald et al. |
| 2009/0221403 | A1 | 9/2009 | Chan et al. |
| 2009/0305732 | A1 | 12/2009 | Marcellino et al. |
| 2009/0305744 | A1 | 12/2009 | Ullrich |
| 2009/0307619 | A1 | 12/2009 | Gupta et al. |
| 2009/0320047 | A1 | 12/2009 | Khan et al. |
| 2010/0015584 | A1 | 1/2010 | Singer et al. |
| 2010/0024531 | A1 | 2/2010 | Senoo |
| 2010/0076278 | A1 | 3/2010 | van der Zande et al. |
| 2010/0085841 | A1 | 4/2010 | Lazaridis et al. |
| 2010/0105525 | A1 | 4/2010 | Thukral et al. |
| 2010/0159995 | A1 | 6/2010 | Stallings et al. |
| 2010/0185064 | A1 | 7/2010 | Bandic et al. |
| 2010/0188328 | A1 | 7/2010 | Dodge et al. |
| 2010/0210975 | A1 | 8/2010 | Anthony, III et al. |
| 2010/0245078 | A1 | 9/2010 | Nadkarni et al. |
| 2010/0295684 | A1 | 11/2010 | Hsieh et al. |
| 2010/0331145 | A1 | 12/2010 | Lakovic et al. |
| 2010/0331147 | A1 | 12/2010 | Mikan et al. |
| 2011/0010617 | A1 | 1/2011 | Kim et al. |
| 2011/0032105 | A1 | 2/2011 | Hoffman et al. |
| 2011/0082007 | A1 | 4/2011 | Birrell et al. |
| 2011/0092282 | A1 | 4/2011 | Gary |
| 2011/0109540 | A1 | 5/2011 | Milne et al. |
| 2011/0152696 | A1 | 6/2011 | Ryan |
| 2011/0154196 | A1 | 6/2011 | Icho et al. |
| 2011/0213473 | A1 | 9/2011 | Vitolo et al. |
| 2011/0252362 | A1 | 10/2011 | Cho et al. |
| 2011/0267196 | A1 | 11/2011 | Hu et al. |
| 2012/0010478 | A1 | 1/2012 | Kinnunen et al. |
| 2012/0041767 | A1 | 2/2012 | Hoffman et al. |
| 2012/0059664 | A1 | 3/2012 | Georgiev et al. |
| 2012/0060123 | A1 | 3/2012 | Smith |

(56) References Cited

U.S. PATENT DOCUMENTS

| | | |
|---|---|---|
| 2012/0077641 A1 | 3/2012 | Dyer et al. |
| 2012/0078127 A1 | 3/2012 | McDonald et al. |
| 2012/0083715 A1 | 4/2012 | Yuen et al. |
| 2012/0084053 A1 | 4/2012 | Yuen et al. |
| 2012/0092383 A1 | 4/2012 | Hysek et al. |
| 2012/0108215 A1 | 5/2012 | Kameli |
| 2012/0112908 A1 | 5/2012 | Prykari et al. |
| 2012/0116550 A1 | 5/2012 | Hoffman et al. |
| 2012/0129138 A1 | 5/2012 | Redmann |
| 2012/0159218 A1 | 6/2012 | Vangala et al. |
| 2012/0246246 A1 | 9/2012 | Moore |
| 2012/0252416 A1 | 10/2012 | Kissinger et al. |
| 2012/0253485 A1 | 10/2012 | Weast et al. |
| 2012/0258433 A1 | 10/2012 | Hope et al. |
| 2012/0274508 A1 | 11/2012 | Brown et al. |
| 2012/0277605 A1 | 11/2012 | Colborn |
| 2012/0291544 A1 | 11/2012 | Kawabe |
| 2012/0303319 A1 | 11/2012 | Kirkeby |
| 2012/0316896 A1 | 12/2012 | Rahman et al. |
| 2012/0326873 A1 | 12/2012 | Utter, II |
| 2013/0007665 A1 | 1/2013 | Chaudhri et al. |
| 2013/0013331 A1 | 1/2013 | Horseman |
| 2013/0017891 A1 | 1/2013 | Romero et al. |
| 2013/0067014 A1 | 3/2013 | Lau et al. |
| 2013/0072823 A1 | 3/2013 | Kahn et al. |
| 2013/0078958 A1 | 3/2013 | Kyprianou |
| 2013/0080811 A1 | 3/2013 | Low et al. |
| 2013/0090881 A1 | 4/2013 | Janardhanan et al. |
| 2013/0106603 A1 | 5/2013 | Weast et al. |
| 2013/0106684 A1 | 5/2013 | Weast et al. |
| 2013/0117381 A1 | 5/2013 | Garcia et al. |
| 2013/0119255 A1 | 5/2013 | Dickinson et al. |
| 2013/0122928 A1 | 5/2013 | Pfluger |
| 2013/0123959 A1 | 5/2013 | Kan et al. |
| 2013/0138734 A1 | 5/2013 | Crivello et al. |
| 2013/0157646 A1 | 6/2013 | Ferren et al. |
| 2013/0178334 A1 | 7/2013 | Brammer |
| 2013/0197681 A1 | 8/2013 | Alberth, Jr. et al. |
| 2013/0198685 A1 | 8/2013 | Bernini et al. |
| 2013/0205306 A1 | 8/2013 | Kelly |
| 2013/0234924 A1 | 9/2013 | Janefalkar et al. |
| 2013/0237874 A1 | 9/2013 | Zoicas |
| 2013/0241718 A1 | 9/2013 | Wang et al. |
| 2013/0254525 A1 | 9/2013 | Johnson et al. |
| 2013/0271392 A1 | 10/2013 | Lyons |
| 2013/0290879 A1 | 10/2013 | Greisson |
| 2013/0293494 A1 | 11/2013 | Reshef |
| 2013/0310896 A1 | 11/2013 | Mass |
| 2013/0324368 A1 | 12/2013 | Aragones et al. |
| 2013/0325491 A1 | 12/2013 | Ferrari |
| 2014/0066816 A1 | 3/2014 | McNames et al. |
| 2014/0070957 A1 | 3/2014 | Longinotti-Buitoni et al. |
| 2014/0099614 A1 | 4/2014 | Hu et al. |
| 2014/0143064 A1* | 5/2014 | Tran ............... A61B 5/0022 705/14.66 |
| 2014/0143737 A1 | 5/2014 | Mistry et al. |
| 2014/0169675 A1 | 6/2014 | King et al. |
| 2014/0176335 A1 | 6/2014 | Brumback et al. |
| 2014/0176346 A1 | 6/2014 | Brumback et al. |
| 2014/0176422 A1 | 6/2014 | Brumback et al. |
| 2014/0180595 A1 | 6/2014 | Brumback et al. |
| 2014/0197946 A1 | 7/2014 | Park et al. |
| 2014/0197963 A1 | 7/2014 | Park et al. |
| 2014/0197965 A1 | 7/2014 | Park et al. |
| 2015/0042471 A1 | 2/2015 | Park et al. |
| 2015/0091812 A1 | 4/2015 | Sood et al. |
| 2015/0094831 A1 | 4/2015 | Brumback et al. |
| 2015/0094832 A1 | 4/2015 | Brumback et al. |
| 2015/0231446 A1 | 8/2015 | Brumback et al. |
| 2015/0245801 A1 | 9/2015 | Brumback et al. |
| 2015/0294554 A1 | 10/2015 | Park et al. |

FOREIGN PATENT DOCUMENTS

| | | |
|---|---|---|
| EP | 1 721 237 | 8/2012 |
| WO | WO 2011/139671 | 11/2011 |
| WO | WO 2012/170366 | 12/2012 |
| WO | WO 2013/040674 | 3/2013 |
| WO | WO 2013/093011 | 6/2013 |
| WO | WO 2013/169755 | 11/2013 |

OTHER PUBLICATIONS

US Final Office Action, dated Jul. 8, 2015, issued in U.S. Appl. No. 14/029,763.
US Office Action, dated Feb. 5, 2014, issued in U.S. Appl. No. 14/045,563.
US Final Office Action, dated Jul. 28, 2014, issued in U.S. Appl. No. 14/045,563.
US Office Action, dated Jul. 17, 2015, issued in U.S. Appl. No. 14/045,563.
US Final Office Action, dated Jan. 4, 2016, issued in U.S. Appl. No. 14/045,563.
US Office Action, dated Apr. 4, 2014, issued in U.S. Appl. No. 14/045,574.
US Final Office Action, dated Jul. 31, 2014, issued in U.S. Appl. No. 14/045,574.
US Advisory Action, dated Nov. 17, 2014, issued in U.S. Appl. No. 14/045,574.
US Notice of Allowance, dated Jan. 14, 2015, issued in U.S. Appl. No. 14/045,574.
US Notice of Allowance, dated Apr. 8, 2015, issued in U.S. Appl. No. 14/045,574.
US Office Action, dated Jan. 8, 2014, issued in U.S. Appl. No. 14/045,592.
US Notice of Allowance, dated Apr. 25, 2014, issued in U.S. Appl. No. 14/045,592.
US Office Action, dated Apr. 10, 2015, issued in U.S. Appl. No. 14/029,759.
US Office Action, dated Mar. 27, 2014, issued in U.S. Appl. No. 14/062,717.
US Notice of Allowance, dated Jul. 8, 2014, issued in U.S. Appl. No. 14/062,717.
US Notice of Allowance, dated Sep. 5, 2014, issued in U.S. Appl. No. 14/062,717.
US Office Action, dated Jan. 16, 2015, issued in U.S. Appl. No. 14/524,909.
US Notice of Allowance, dated Nov. 6, 2015, issued in U.S. Appl. No. 14/524,909.
US Office Action, dated Dec. 30, 2013, issued in U.S. Appl. No. 14/029,760.
US Final Office Action, dated Apr. 8, 2014, issued in U.S. Appl. No. 14/029,760.
US Office Action, dated Jul. 23, 2014, issued in U.S. Appl. No. 14/029,760.
US Final Office Action, dated Dec. 4, 2014, issued in U.S. Appl. No. 14/029,760.
US Notice of Allowance, dated Mar. 24, 2015, issued in U.S. Appl. No. 14/029,760.
US Office Action, dated Sep. 24, 2015, issued in U.S. Appl. No. 14/749,386.
US Final Office Action, dated Apr. 28, 2016, issued in U.S. Appl. No. 14/749,386.
US Office Action, dated Dec. 24, 2013, issued in U.S. Appl. No. 14/050,166.
US Applicant-Initiated Interview Summary dated Mar. 11, 2014, issued in U.S. Appl. No. 14/050,166.
US Notice of Allowance, dated Apr. 8, 2014, issued in U.S. Appl. No. 14/050,166.
US Office Action, dated Jul. 29, 2014, issued in U.S. Appl. No. 14/261,344.
US Office Action, dated Jan. 14, 2014, issued in U.S. Appl. No. 14/050,182.
US Applicant Initiated Interview Summary, dated Mar. 7, 2014, issued in U.S. Appl. No. 14/050,182.

(56) References Cited

OTHER PUBLICATIONS

US Final Office Action, dated May 1, 2014, issued in U.S. Appl. No. 14/050,182.
US Applicant Initiated Interview Summary, dated Aug. 19, 2014, issued in U.S. Appl. No. 14/050,182.
US Notice of Allowance, dated Nov. 14, 2014, issued in U.S. Appl. No. 14/050,182.
US Office Action, dated Jun. 20, 2014, issued in U.S. Appl. No. 14/261,347.
US Office Action, dated Jul. 29, 2014, issued in U.S. Appl. No. 14/261,347.
US Final Office Action, dated Nov. 26, 2014, issued in U.S. Appl. No. 14/261,347.
US Notice of Allowance, dated Feb. 5, 2015, issued in U.S. Appl. No. 14/261,347.
US Office Action, dated Aug. 14, 2015, issued in U.S. Appl. No. 14/712,501.
US Final Office Action, dated Nov. 24, 2015, issued in U.S. Appl. No. 14/712,501.
US Advisory Action, dated Mar. 1, 2016, issued in U.S. Appl. No. 14/712,501.
US Office Action, dated Jun. 24, 2014, issued in U.S. Appl. No. 14/261,349.
US Final Office Action, dated Oct. 10, 2014, issued in U.S. Appl. No. 14/261,349.
US Notice of Allowance, dated Dec. 24, 2014, issued in U.S. Appl. No. 14/261,349.
US Notice of Allowance (Corrected Notice of Allowability), dated Apr. 1, 2015, issued in U.S. Appl. No. 14/261,349.
Chinese First Office Action dated Oct. 20, 2015 issued in CN 201410475447.4.
"Activator is One of the Best Cydia iPhone Hacks | Control your iPhone with Gestures," iphone-tips-and-advice.com, [retrieved on Jul. 9, 2013 at http://www.iphone-tips-and-advice.com/activatior. html], 10 pp.
Ali-Hasan, N., Gavales, D., Peterson, A. & Raw, M., (Apr. 22-27, 2006) "Fitster: Social Fitness Information Visualizer," *in Ext. Abstr. Hum. Factors Comput. Syst., ACM Press*, 1795-1800.
Anderson, Ian et al. (Aug. 3, 2007) "Shakra: Tracking and Sharing Daily Activity Levels with Unaugmented Mobile Phones," *Mobile Networks Appl.* 12:185-199.
Bonato, P. (May/Jun. 2010) "Wearable Sensors and Systems," *IEEE Eng. in Medicine and Biology Magazine*, 29:25-36.
Buttussi, F. & Chittaro, L. (2008) "MOPET, A context-aware and user-adaptive wearable system for fitness training," *Artificial Intelligence in Medicine*, 42:153-163.
Chudnow, Alan (Dec. 3, 2012) "Basis Wristband Make Its Debut," *The Wired Self, Living in a Wired World*, published in Health [retrieved on Jul. 22, 2013 at http://thewiredself.com/health/basis-wrist-band-make-its-debut/], 3pp.
Consolvo, S., Everitt, K., Smith, I. & Landay, J.A. (Apr. 22-27, 2006) "Design Requirements for Technologies that Encourage Physical Activity," CHI 2006 Proceedings, Designing for Tangible Interactions, *In Hum. Factors Comput. System, ACM Press*, 457-466.
DesMarais, Christina (posted on Sep. 3, 2013) "Which New Activity Tracker is Best for You?" *Health and Home, Health & Fitness, Guides & Reviews*, [Retrieved on Sep. 23, 2013 at http://www.techlicious.com/guide/which-new-activity-tracker-is-right-for-you/] 4 pp.
Dobkin, B. H. & Dorsch, A. (2011) "The Promise of mHealth: Daily Activity Monitoring and Outcome Assessments by Wearable Sensors," *Neurorehabilitation and Neural Repair*, 25(9):788-98.
Empson, Rip, (Sep. 22, 2011) "Basis Reveals an Awesome New Affordable Heart and Health Tracker You Can Wear on Your Wrist," [retrieved on Sep. 23, 2013 at http ://techcrunch.com/2011/09/22/basis-reveals-an-awesome-new . . . ], 3 pp.
Fitbit User's Manual, Last Updated Oct. 22, 2009, 15 pages.
Forerunner® 10 Owner's Manual (Aug. 2012), Garmin Ltd., 10 pp.

Forerunner® 110 Owner's Manual, (2010) "GPS-Enabled Sport Watch," Garmin Ltd., 16 pp.
Forerunner® 201 personal trainer owner's manual, (Feb. 2006) Garmin Ltd., 48 pp.
Forerunner® 205/305 Owner's Manual, GPS-enabled trainer for runners, (2006-2008), Garmin Ltd., 80 pp.
Forerunner® 210 Owner's Manual, (2010) "GPS-Enabled Sport Watch," Garmin Ltd., 28 pp.
Forerunner® 301 personal trainer owner's manual, (Feb. 2006) Garmin Ltd., 66 pp.
Forerunner® 310XT Owner's Manual, Multisport GPS Training Device, (2009-2013), Garmin Ltd., 56 pp.
Forerunner® 405 Owner's Manual, (Mar. 2011) "GPS-Enabled Sport Watch With Wireless Sync," Garmin Ltd., 56 pp.
Forerunner® 405CX Owner's Manual, "GPS-Enabled Sports Watch With Wireless Sync," (Mar. 2009), Garmin Ltd., 56 pp.
Forerunner® 410 Owner's Manual, (Jul. 2012) "GPS-Enabled Sport Watch With Wireless Sync," Garmin Ltd., 52 pp.
Forerunner® 50 with ANT+Sport™ wireless technology, Owner's Manual, (Nov. 2007) Garmin Ltd., 44 pp.
Forerunner® 910XT Owner's Manual, (Jan. 2013) Garmin Ltd., 56 pp.
Gamelin, F.X., Berthoin, S. & Bosquet, L. (2006) "Validity of the Polar S810 Heart Rate Monitor to Measure R-R Intervals at Rest," *Med. Sci. Sports Exerc.* 38(5):887-893.
Garmin Swim™Owner's Manual (Jun. 2012), 12 pp.
Gomes, N. et al. (2012) "Steptacular: An incentive mechanism for promoting wellness," *in Conf. Commun. Syst. Networks, IEEE*, 1-6.
Gupta, N. & Jilla, S. (2011) "Digital Fitness Connector: Smart Wearable System," First *International Conference on Informatics and Computational Intelligence, IEEE Computer Society*, 118-121.
Kranz, M. et al. (2013) "The mobile fitness coach: Towards individualized skill assessment using personalized mobile devices," *Pervasive Mob. Computing*, 9:203-215.
Lane, N. et al. (2010) "A survey of mobile phone sensing," *IEEE Communications Magazine*, 48:140-150.
Lark/Larkpro, User Manual, (2012) "What's in the box," *Lark Technologies*, 7 pp.
Larklife, User Manual, (2012) *Lark Technologies*, 7 pp.
Le Masurier, G. C. & Tudor-Locke, C. (2003) "Comparison of Pedometer and Accelerometer Accuracy under Controlled Conditions," *Med.& Sci. in Sports & Exerc.* 35:867-871.
Marschollek, M. et al. (Aug. 20-24, 2008) "A performance comparison of accelerometry-based step detection algorithms on a large, non-laboratory sample of healthy and mobility-impaired persons," *30th Annual International IEEE EMBS Conference, Vancouver, BC, Canada, Eng. Med. Biol. Mag.* 1319-1322.
Milošević, M., Shrove, M. T. & Jovanov, E. (Jun. 2011) "Applications of Smartphones for Ubiquitous Health Monitoring and Wellbeing Management," *Journal of Information Technology and Applications*, 1:7-15.
Nike+ FuelBand GPS Manual, User's Guide (Product Release Date Unknown, downloaded Jul. 22, 2013), 26 pages.
Nike+SportBand User's Guide, (Product Release Date Unknown, downloaded Jul. 22, 2013), 36 pages.
Nike+SportWatch GPS Manual, User's Guide, Powered by TOMTOM, (Product Release Date Unknown, downloaded Jul. 22, 2013), 42 pages.
"Parts of Your Band," (Product Release Date Unknown, downloaded Jul. 22, 2013) Jawbone UP Band, 1 page.
Polar WearLink® + Coded Transmitter 31 Coded Transmitter W.I.N.D. User Manual, Polar® Listen to Your Body, *Manufactured by Polar Electro Oy*, (2010) 11 pages.
Rainmaker, (Jun. 25, 2012, updated Feb 16, 2013) "Garmin Swim watch In-Depth Review," [retrieved on Sep. 9, 2013 at http://www.dcrainmaker.com/2012/06/garmin-swim-in-depth-review.html, 38 pp.
Schloesser, M., Schnitzer, A., Ying, H., Silex, C. & Schiek, M. (Aug. 20-24, 2008) "iSANLA: intelligent Sensor and Actuator Network for Life science Applications," *i 30th Annual International IEEE EMBS Conference, Vancouver, BC, Canada, Med. Biol. Soc.* 2369-2372.

(56) References Cited

OTHER PUBLICATIONS

Schneider, P.L., Crouter, S. E. & Bassett, D. R. (2004) "Pedometer Measures of Free-Living Physical Activity: Comparison of 13 Models," *Med.& Sci. in Sports & Exerc.* 36(2): 331-335.

Tudor-Locke, C., Ainsworth, B.E., Thompson, R.W. & Matthews, C.E. (2002) Comparison of pedometer and accelerometer measures of free-living physical activity, *Med. Sci. Sports Exerc.* 34(12):2045-2051.

Tudor-Locke, C. et al. (Mar.-Apr. 2006) "Evaluation of Quality of Commercial Pedometers," *Can. J Public Heal.* 97(1):S10-S15.

Ying, H., Silex, C., Schnitzer, A., Leonhardt, S. & Schiek, M. (Springer Berlin Heidelberg, 2007) "Automatic Step Detection in the Accelerometer Signal," *in Wearable Implant Body Sens. Networks* (Leonhardt, S., Falck, T. & Mahonen, P.) 13:80-85.

Zichermann, G. & Cunningham, C. (2011) "Gamification by Design, Implementing Game Mechanics in Web and Mobile Apps," *O'Reilly Media*, Excerpt of pp. 55-58.

\* cited by examiner

PORTABLE MONITORING DEVICES AND METHODS OF OPERATING THE SAME

CROSS REFERENCE TO RELATED APPLICATIONS

This application is a Continuation of co-pending and commonly assigned U.S. patent application Ser. No. 14/524,909 filed 27 Oct. 2014 and titled "PORTABLE MONITORING DEVICES AND METHODS OF OPERATING THE SAME," which is a Continuation of commonly assigned U.S. patent application Ser. No. 14/062,017 filed 24 Oct. 2013 and titled "PORTABLE MONITORING DEVICES AND METHODS OF OPERATING THE SAME," which is a Continuation of commonly assigned U.S. patent application Ser. No. 14/029,759 filed 17 Sep. 2013 and titled "PORTABLE MONITORING DEVICES AND METHODS OF OPERATING THE SAME," which claims priority to U.S. Provisional Patent Application No. 61/830,600 filed 3 Jun. 2013 and titled "PORTABLE MONITORING DEVICES AND METHODS OF OPERATING SAME," and which claims priority to U.S. Provisional Application No. 61/752,826 filed 15 Jan. 2013 and titled "PORTABLE MONITORING DEVICES AND METHODS OF OPERATING SAME," all of which applications are hereby incorporated by reference herein in their entireties and for all purposes.

BACKGROUND

Increasing consumer interest in personal health has resulted in the development of a variety of personal health monitoring devices. Such devices have tended to be complicated to use or typically designed for use with only one activity: for example, running or bicycling, but not both. Relatively recent advances in the miniaturization of sensors, power sources, and other electronics or components have enabled personal health monitoring devices to be offered in smaller sizes, form factors, or shapes than were previously feasible or industrially practical. For example, the Fitbit Ultra (manufactured by Fitbit Inc. headquartered in San Francisco, Calif.) is a biometric monitoring device that is approximately 2" long, 0.75" wide, and 0.5" deep. The Fitbit Ultra has a pixelated display, battery, sensors, wireless communications capability, power source, and interface button, as well as an integrated clip for attaching the device to a pocket or other portion of clothing, all packaged within this small volume.

SUMMARY

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale unless specifically indicated as being scaled drawings.

In one aspect of the disclosed implementations, a device includes one or more motion sensors for sensing motion of the device and providing activity data indicative of the sensed motion. The device also includes one or more processors for monitoring the activity data, and receiving or generating annotation data for annotating the activity data with one or more markers or indicators to define one or more characteristics of an activity session. The device also includes one or more feedback devices for providing feedback, a notice, or an indication to a user based on the monitoring. The device further includes a portable housing that encloses at least portions of the motion sensors, the processors and the feedback devices.

In some implementations, the device further includes a memory and the processors are further configured to store the activity data or data derived from the activity data in the memory. In some such implementations, the processors are further configured to store the annotation data in the memory. In some implementations, the processors are further configured to determine one or more activity metrics based on the activity data. In some such implementations, the processors are further configured to determine one or more activity metrics based on the annotation data.

In some implementations, the device further includes one or more user input devices included in or on the housing for receiving or sensing user input, and the processors are further configured to receive and interpret the user input received or sensed via the user input devices. In some such implementations, the motion sensors themselves also can function as user input devices by sensing a user's touch, tapping, or other physical gesture made on or with the device. In some implementations, the device further includes transmitting and receiving circuitry. In some such implementations, the user input is input by the user via an external or remote device and then communicated to the receiving circuitry. In some such implementations, the processors are further configured to receive and interpret the user input received from the receiving circuitry. In some such implementations, the transmitting and receiving circuitry is configured for wireless communication over a computer network, and the user input is input via a web or mobile application.

In some implementations, the device is configured to enable a user to input the annotation data via user input. In some such implementations, the user input is input based on a physical interaction with the device that is then interpreted by the processors. In some other implementations, the user input is input to an external device that is communicatively-coupled with the device via one or more wired or wireless connections or networks. In some implementations, the device is configured to enable a user to initiate, indicate, or mark a start time or an end time of a user-defined activity session in response to user input received via one the one or more user interface devices. In some implementations, the device is configured to enable a user to indicate a particular user activity performed during a user-defined activity session in response to user input received via one the one or more user interface devices.

In some implementations, the device is configured to automatically annotate the activity data or to generate the annotation data. In some such implementations, the device is configured to automatically annotate the activity data or to generate the annotation data based on a device state. In some implementations, the device is configured to automatically annotate the activity data or to generate the annotation data based on an analysis of the activity data. In some implementations, the processors are configured to automatically determine the activity data to track or the activity metrics to calculate based on the annotation data.

In some implementations, the housing includes a wrist- or arm-band, is configured for physical attachment to or coupling with a wrist- or arm-band, or is configured to be inserted into a wrist- or arm-band. In some implementations, the device further includes one or more of: one or more gyroscopes, one or more physiological sensors, one or more biometric sensors, one or more altitude sensors, one or more temperature sensors, and one or more heart-rate sensors.

In another aspect of the disclosed implementations, a method of monitoring one or more activity metrics using a portable monitoring device is described. In some implementations, the method includes sensing, by one or more motion sensors within the device, motion of the device. The method also includes outputting, by the one or more motion sensors, activity data indicative of the sensed movement. The method also includes receiving, by one or more processors within the device, the activity data. The method additionally includes receiving or generating, by the one or more processors, annotation data. The method further includes annotating the activity data based on the annotation data.

In some implementations, the method further includes receiving the annotation data from a user. In some other implementations, the method includes generating the annotation data based on the activity data. In some implementations, the processors are further configured to determine or calculate one or more activity metrics based on the activity data and the annotation data.

In still another aspect of the disclosed implementations, a device includes one or more motion sensors for sensing motion of the device and providing activity data indicative of the sensed motion. The device also includes one or more processors for monitoring the activity data, and for switching among a plurality of activity-tracking modes. The device also includes one or more feedback devices for providing feedback, a notice, or an indication to a user based on the monitoring. The device further includes a portable housing that encloses at least portions of the motion sensors, the processors and the feedback devices.

In some implementations, the processors are further configured to determine one or more activity metrics based on the activity data. In some implementations, the processors are further configured to determine the one or more activity metrics based on which of the activity-tracking modes is currently active. In some implementations, the device is configured to enable a user to set or select a particular activity-tracking mode to switch into based on user input. In some implementations, the device is configured to automatically determine or select a particular activity-tracking mode to switch into in response to the activity data. In some implementations, the plurality of activity-tracking modes include one or more activity-specific activity-tracking modes and a sleep-tracking mode.

BRIEF DESCRIPTION OF THE DRAWINGS

The various implementations disclosed herein are illustrated by way of example, and not by way of limitation, in the figures of the accompanying drawings, in which like reference numerals may refer to similar elements.

DETAILED DESCRIPTION

Figure 1:
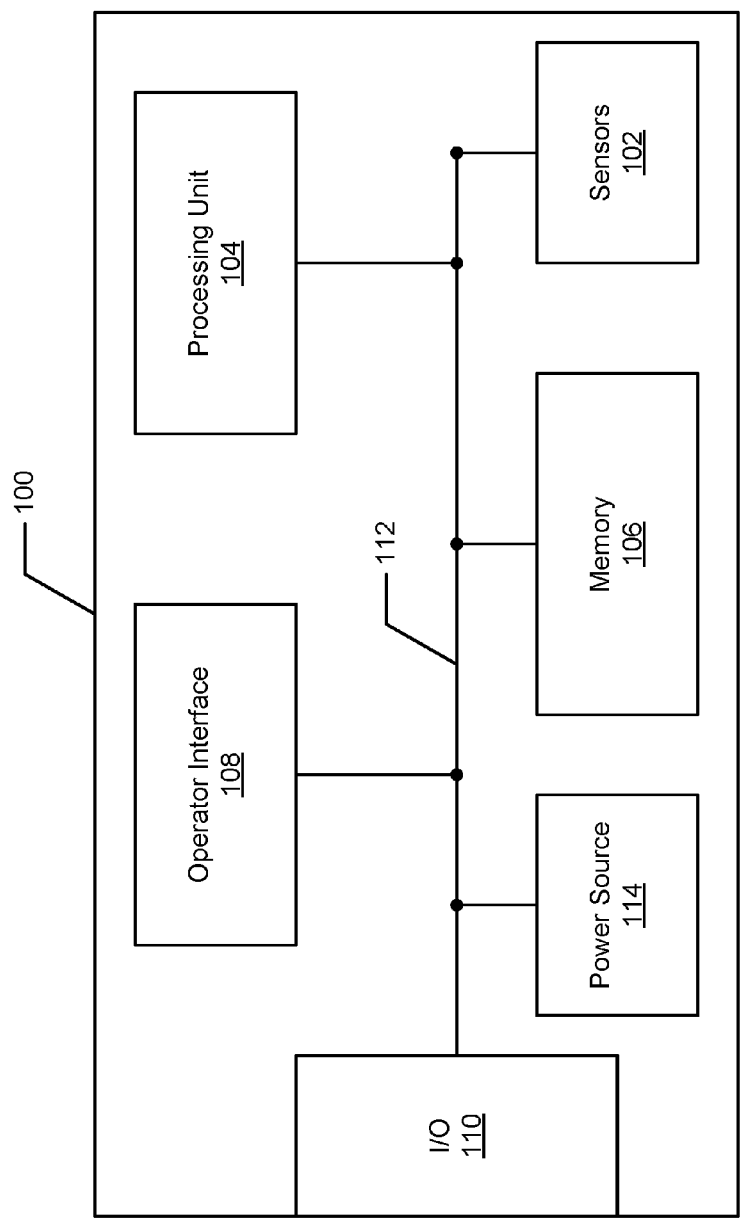
FIG. 1 depicts a block diagram of an example portable monitoring device.

The present disclosure relates generally to portable monitoring devices (also referred to herein as "portable tracking devices" or simply as "devices"), and more particularly, to wearable monitoring devices including wearable biometric monitoring devices. Various implementations relate to a portable monitoring device capable of monitoring and tracking movements or activities and related data. For example, the portable monitoring device can include one or more motion sensors for detecting movement data or various other biometric, physiological, or environmental sensors for detecting biometric data, physiological data, environmental data, or related data (hereinafter also collectively referred to as "activity data"). In some example implementations, the portable monitoring device includes a general or default activity-tracking mode. In some such implementations, the default activity-tracking mode is an "annotation mode." In some such implementations, the activity data monitored or tracked (hereinafter "monitored" and "tracked" may be used interchangeably) while in the annotation mode can be annotated or otherwise marked to indicate, specify, or delineate the starting and ending time points, a duration, or other time points of or within an activity session.

For purposes of this disclosure, an "activity session" may generally refer to a user-defined duration of time, or a duration of time associated with a particular activity or time of day, in which the device is monitoring activity data. In some implementations, the activity data monitored while in the default annotation mode also can be annotated or otherwise marked to indicate, specify, or define a specific activity that is being performed by the user during the activity session such as, for example, walking, running, stair climbing, bicycling, swimming, or even sleeping. In various implementations, the user can annotate the activity data prior to, during, or after completion of an associated activity. In various implementations, one or more activity metrics can be determined, calculated, or analyzed based on the activity data. In some such implementations, the activity metrics are communicated to the user via a display, lighting, noise, or via vibrational or haptic feedback. In some implementations, one or more achieved goals, progress indicators, alerts, or other activity-based notifications may be communicated to the user based on one or more of the activity metrics. Additionally or alternatively, in some implementations, one or more alarms, reminders, or other time-, physiologically-, biometrically-, state-, condition-, or environment-based notifications also can be communicated to the user. Such achieved goals, progress indicators, alerts, or other notifications can be communicated to the user via a display, lighting, noise, or via vibrational or haptic feedback.

In some other implementations, the portable monitoring device is capable of switching among two or more modes such as two or more activity-tracking modes. In some such implementations, the two or more activity-tracking modes include one or more activity-specific activity-tracking modes including, for example, a walking mode, a running mode, a stair-climbing mode, a bicycling mode, a swimming mode, a climbing mode, and a golfing mode, among other example activity-tracking modes configured for other corresponding activities. In some implementations, the two or more activity-tracking modes also can include a sleep-tracking mode. In some implementations, the portable monitoring device itself can determine which activity data to monitor or which activity (or sleep) metrics (hereinafter "sleep metrics" also may generally be referred to as "activity metrics") to determine, compute, calculate, track or analyze (hereinafter used interchangeably) based on which of the activity-tracking modes is currently active or initiated. Additionally or alternatively, in some implementations, one or both of an external computing device or a back-end server can request certain activity data from the portable monitoring device based on which of the activity-tracking modes is currently active or initiated. Additionally or alternatively, in some implementations, one or both of an external computing device or a back-end server can receive all activity data monitored by the portable monitoring device and subsequently filter or otherwise selectively process certain activity data to determine certain activity (or sleep) metrics based on which of the activity-tracking modes is currently active or initiated.

FIG. 1 depicts a block diagram of an example portable monitoring device 100. The portable monitoring device 100 includes one or more sensors 102. The portable monitoring device 100 also includes a processing unit 104, a memory 106, a user interface 108, and input/output (I/O) interface 110. The one or more sensors 102, the processing unit 104, the memory 106, the user interface 108, and the I/O interface 110 are communicatively connected with one or more of one another via one or more communication paths collectively referred to as communication bus 112. The portable monitoring device 100 further includes a power source 114, such as, for example, one or more rechargeable or a removable batteries.

The sensors 102 include one or more motion sensors configured for sensing and outputting movement data indicative of the motion of the portable monitoring device 100. For example, the motion sensors can include one or more accelerometers for sensing movement data. In some implementations, the portable monitoring device 100 includes one or more accelerometers for sensing acceleration or other movement data in each of, for example, three directions, which may be orthogonal. The sensors 102 additionally can include one or more gyroscopes for sensing rotation data. In some implementations, the portable monitoring device 100 includes one or more gyroscopes for sensing rotation about each of, for example, three axes, which may be orthogonal. As will be described later, movement data and rotation data also can be used to capture user input. The sensors 102 additionally can include one or more altimeters (hereinafter also referred to as "altitude sensors." For example, the portable monitoring device 100 can include a pressure or barometric altimeter. The sensors 102 additionally can include one or more temperature sensors for sensing one or both of a temperature of the environment outside of the user's body or an internal temperature of the user's body. The sensors 102 additionally can include one or more light sensors (for example, photodetectors). For example, the light sensors can be used to detect an ambient light level of the environment for use in, for example, determining a suitable or optimal intensity of a display of the portable monitoring device 100. Other light sensors can be used to gather other biometric data such as an oxygen level of the user's blood. The sensors 102 also can include one or more pressure or proximity sensors for receiving user input. Such pressure or proximity sensors can be based on mechanical designs or on, for example, capacitive, resistive, or other electrical or optical designs. The portable monitoring device 100 also can be coupled with external sensing devices such as an external heart rate monitor (for example, a chest-strap heart rate monitor) for sensing a user's hear rate. The portable monitoring device 100 also can include or be coupled with other physiological or biometric sensors. In some implementations, the portable monitoring device 100 additionally is configured to sense or monitor one or more other types of biometric data or to measure, calculate, or determine biometric data based on the movement, rotation, or other data described above. Biometric data, as used herein, may refer to virtually any data pertaining to the physical characteristics of the human body, and as described above, activity data may also refer to such biometric data.

The processing unit 104 can include one or more processors, processing circuits, computing units, computing circuits, controllers, or microcontrollers (hereinafter used interchangeably). Each of the processors can be implemented by a general- or special-purpose processor (or set of processing cores) and can execute sequences of programmed instructions ("code") to perform tasks and effectuate various operations. Additionally or alternatively, the processing unit 104 can include a custom-built hardware ASIC (application-specific integrated circuit), or can be programmed into a programmable logic device such as an FPGA (field-programmable gate array). In some implementations, the memory 106 stores executable instructions that, when executed by the processing unit 104, cause the processing unit 104 to control one or more of the sensors 102, to sample or extract data received from the sensors 102, to store the received data in the memory 106, and to retrieve or load data previously stored in the memory 106. The activity data received from the sensors 102 may be stored in raw format in the memory 106 by the processing unit 104, or may be pre-processed prior to storage in the memory 106. For example, the processing unit 104 may store or buffer the most recent 10 minutes of activity data in raw form, but may then store data from prior to the ten-minute window as filtered data, for example, with a lower sampling rate or with some form of numerical analysis, such as a moving average, performed, or as converted data: for example, acceleration data may be converted to activity metrics such as "steps taken," "stairs climbed," or "distance traveled."

Activity data from the sensors 102, including raw data or post-processed data, may be further analyzed to determine if the activity data is indicative of a pre-defined biometric state or condition that is associated with a user input. If such analysis indicates that such data has been collected, the processing unit 104 may then treat such an event as equivalent to a user input. In some implementations, the processing unit 104 also may derive secondary data based on the raw activity data. In some implementations, the processing unit 104 also performs an analysis on the raw activity data received from the sensors 102 or on raw or previously-processed ("post-processed") activity data retrieved from the memory 106 and initiates various actions based on the analysis. For example, the processing unit 104 may track, determine, compute, calculate or analyze one or more physiological, biometric, activity or sleep metrics (hereinafter collectively referred to as "activity metrics") based on the raw, pre-processed or secondary activity data (also collectively referred to herein generally as "activity data").

The memory 106 can include any suitable memory architecture. In some implementations, the memory 106 includes different classes of storage devices or units to store different classes of data. In some implementations, the memory 106 includes non-volatile storage media, such as fixed or removable semiconductor-, optical-, or magnetic-based media, for storing executable code (also referred to as "executable instructions") and related data for enabling the implementations and carrying out the processes described herein. In some implementations, the memory 106 also is configured for storing configuration data or other information for implementing various default or user-defined settings, or for implementing the default or activity-specific activity-tracking modes described herein. The memory 106 also can be configured for storing other configuration data used during the execution of various programs or instruction sets or otherwise used to configure the portable monitoring device 100. Additionally, any of the afore-described raw activity data generated by the sensors 102, as well as pre-processed or derived data, can be stored in the non-volatile storage media within the memory 106 for later analysis or other use. Additionally, in some implementations, the activity metrics calculated by the processing unit 104 or received from an external computing device or server also can be stored in the non-volatile storage media within the memory 106 for later analysis, viewing or other use. In some implementations, the memory 106 also includes volatile storage media, such as static or dynamic random-access memory (RAM), for temporarily or non-permanently storing more transient information and other variable data as well as, in some implementations, executable code retrieved from the non-volatile storage media. The volatile storage media may also store any of the afore-described data generated by sensors 102 or data derived from sensed data (for example, including activity- or sleep tracking metrics) for later analysis, later storage in non-volatile media within memory 106, or for subsequent communication over a wired or wireless connection via I/O interface 110. The processing unit 104 can additionally or alternatively include its own volatile memory, such as RAM, for loading executable code from non-volatile memory for execution by the processing unit 104, or for tracking, analyzing, or otherwise processing any of the afore-described data generated by sensors 102 or data derived from sensed data (for example, including activity- or sleep tracking metrics) for later analysis, later storage in non-volatile media within memory 106, or for subsequent communication over a wired or wireless connection via I/O interface 110.

As will be described in more detail below, the processing unit 104 also can be configured to track and determine when the activity data received from the sensors 102 or retrieved from the memory 106, or the activity metrics generated from such activity data, indicate that a goal has been achieved or a progress point has been reached. For example, such a goal can be a specific activity metrics such as a distance, a number of steps, an elevation change, or number of calories burned, among other goals as described in more detail below. The processing unit 104 may then notify the user of the achievement of the goal or progress indicator via the user interface 108. For example, the processing unit 104 may cause a display to show content on the display marking or celebrating the achievement of the goal. Additionally or alternatively, the processing unit 104 may cause one or more lights (for example, LEDs) to light up, flash, change intensity, or otherwise reflect a visual pattern or display that notifies the user of the achievement of the goal. Additionally or alternatively, the processing unit 104 may cause one or more sound-producing devices to alert, beep or otherwise make noise that notifies the user of the achievement of the goal. Additionally or alternatively, the processing unit 104 may cause one or more vibrating devices to vibrate or otherwise provide haptic feedback in the form of one or more vibration patterns and, in some implementations, with differing or varying vibrational characteristics to notify the user of the achievement of particular goals.

In some implementations, user interface 108 collectively refers to and includes one or more user input devices and one or more output devices. The memory 106 also can store executable instructions that, when executed by the processing unit 104, cause the processing unit 104 to receive and interpret user input received via the user interface 108, or to output or communicate information to a user via the user interface 108. In various implementations, the user interface 108 can incorporate one or more types of user interfaces including, for example, visual, auditory, touch, vibration, or combinations thereof. For example, user interface 108 can include one or more buttons in or on a device housing that encloses the processing unit 104, the memory 106 and other electrical or mechanical components of the portable monitoring device 100. The buttons can be based on mechanical designs and electrical designs, and may incorporate, for example, one or more pressure sensors, proximity sensors, resistive sensors, capacitive sensors, or optical sensors. The user interface 108 also can include a touchpad or a touchscreen interface, which may be disposed over or integrated with a display, and which can incorporate these or other types of sensors.

In some implementations, the afore-described motion sensors, gyroscopes, or other sensors also can be used to detect a physical gesture corresponding to a user input. This allows a user to interact with the device using physical gestures. For example, accelerometers and gyroscopes can be used to detect when a user "taps," shakes, rotates, flips or makes other "gestures" with the portable monitoring device. As another example, the portable monitoring device 100 can include a magnetometer, which may be used to detect the device's orientation with respect to the Earth's magnetic field. Other gestures that may be used to cause the portable monitoring device 100 to perform some action include, but are not limited to, multiple taps, or a specific pattern of taps. For example, a user may tap anywhere on the exterior (for example, the housing) of the portable monitoring device two times within a specific time period to cause the display to show particular content, to annotate activity data, or to change device modes.

As just described, the user interface 108 also can include a display can be included on or in the housing that encloses the processing unit 104 and the memory 106. In various implementations, the display can be configured as an alphanumeric display, transiently-visible display, or dead-front display. The display also can include or be based on any suitable display technology including liquid crystal display (LCD) technology or light-emitting diode (LED) technology among other suitable display technologies. The display can be configured to display various information to a user. In some implementations, a user can input a selection, navigate through a menu, or input other information via a button, a pressure sensor, a proximity sensor, a resistive sensor, a capacitive sensor, an optical sensor, or a touchscreen incorporating these or other types of sensors.

In various implementations, the display can show activity data, biometric data, contextual data, environmental data, system or intrinsic condition data, or data derived from activity or other sensed data, one or more activity metrics, one or more sleep metrics, a currently-active activity-tracking mode, one or more menus, one or more settings, one or more alarms or other indicators, a clock, a timer, a "stopwatch," among other suitable information. In some implementations, the information that is displayed is customizable by the user or, additionally or alternatively, dependent on a current device state or mode of the portable monitoring device 100. For example, as a consequence of limited display space (to keep the portable monitoring device as small, portable or wearable as possible without sacrificing functionality or ease of use), the data displayed in association with each device state or mode may be partitioned into a plurality of different data display pages, and a user may "advance" through the data display pages associated with a given device state or mode by providing input to the biometric monitoring device.

The term "data display page" as used herein may refer to a visual display including text, graphics, and/or indicators, e.g., LEDs or other lights such as are used on the Fitbit Flex, that are arranged to communicate data measured, produced, or received by a portable monitoring device 100 to a user viewing a display of the portable monitoring device. In order to more dynamically change the display or the notifications provided to a user, the portable monitoring device 100 may track its device state through a variety of mechanisms and transition through different device states as contextual states, environmental states, or modes change. In some implementations, the device may include and be capable of operating in multiple active modes, multiple active environmental states, multiple active contextual states, or combinations of these, simultaneously. In such a case, the device state may be different for each different combination of environmental states, contextual states, or modes.

In implementations that include an annotation mode, an annotation data display page may indicate that the portable monitoring device 100 is in annotation mode. When the portable monitoring device 100 is in the annotation mode (or said differently, when the annotation mode is active or initiated), information related to the activity being annotated may be displayed. For example, data display pages for various types of activity data or activity metrics may show quantities measured while the portable monitoring device 100 is in the annotation mode. For example, while operating in the annotation mode, a data display page for "steps taken" may only display a quantity of steps that have been taken while the portable monitoring device 100 is in the annotation mode or in an activity session defined using annotation data (rather than, for example, the quantity of steps taken throughout the entire day, week, month, year or during the lifetime of the device).

In an example implementation, if the portable monitoring device 100 is in a device state associated with the wearer being asleep (for example, an annotated sleep-tracking state or a sleep-tracking mode), it may be less likely for the wearer to input information into or otherwise interact with the portable monitoring device. Thus, in some implementations, the processing unit 104 may decrease the sensitivities of various user input detection mechanisms, especially a touchscreen, (or turn the display or the entire device completely off) to reduce the risk of accidental inputs or to save power. In other device states, it may be desirable to change the user input method based on the limitations of various input mechanisms in various environments. For example, if the portable monitoring device 100 determines that it is in a device state associated with swimming (for example, the portable monitoring device 100 can be configured to independently determine through moisture sensors or pressure sensor data that it is in water), or if the portable monitoring device is actively placed into a swimming mode by the user via the user interface 108, then, in some implementations, a touchscreen interface or other user interface of the portable monitoring device 100 may be deactivated since it may not function well in water. The wearer may instead interact with the portable monitoring device 100 using physical buttons or other appropriate or suitable input mechanisms, including physical gesutres sensed by the device.

In additional to a display, the portable monitoring device 100, and particularly the user interface 108, also can include other mechanisms to provide feedback or other information to a user. For example, the user interface 108 can include one or more lights, such as one or more LEDs, in addition to the display for communicating information, such as the achievement of a goal, an alarm, an alert, indicator or other notification, a current state, a current mode, or a power level, to the user. For example, the processing unit 104 can control the intensities, colors, or patterns of flashing of one or more of the LEDs of the user interface 108 based on what information is being communicated. In some implementations, the user interface 108 additionally or alternatively includes one or more speakers or sound-producing devices. The user interface 108 also can include one or more microphones or other audio devices.

In some implementations, the user interface 108 includes one or more vibramotors (also referred to herein as "vibrators" or simply as "vibrating devices") for communicating information with or to the user. For example, the processing unit 104 can utilize the vibramotors to communicate one or more alarms, achieved goals, progress indicators, inactivity indicators, reminders, indications that a timer has expired, or other indicators, feedback or notifications to a user wearing or holding the portable monitoring device 100. In some such implementations, the portable monitoring device 100 can utilize the vibramotors to communicate such information to the user in addition to communicating the same or similar information via the display, the lights, or the sound-producing devices. In some other such implementations, the portable monitoring device 100 can utilize the vibramotors to communicate such information to the user instead of or in lieu of communicating the same or similar information via the display, the lights, or the sound-producing devices. For example, in the case of an alarm, the vibramotors can cause the portable monitoring device 100 to vibrate to wake the user from sleep while not making noise so as to not wake the user's partner. As another example, in the case of a goal-achievement or progress indicator, the vibramotors can cause the portable monitoring device 100 to vibrate to alert the user that the user's goal has been achieved or that a milestone or other progress point en route to the goal has been reached without requiring the user to look at a display or hear an indication output from a speaker. In some implementations, a user can define one or more custom vibration patterns or other vibrational characteristics and assign such differing vibration patterns or other vibrational characteristics to different alarms, goals, or other vibrating indicators so that the user can distinguish among the vibrating indicators to determine what information is being communicated by the portable monitoring device 100. Additionally or alternatively, in some implementations, a user can select one or more default vibration patterns or other vibrational characteristics stored in the memory 106 and assign such differing vibration patterns or other vibrational characteristics to various vibrating indicators. In various implementations, the user can customize such patterns, characteristics, or settings or make such selections via the user interface 108, or via an application or program (including a web application, mobile application, or client-side software program) executing on an external computing device (for example, a personal computer, smartphone or multimedia device) communicatively coupled with the portable monitoring device 100 via the I/O interface 110 and one or more wired or wireless connections or networks.

In some implementations, as described above, one or more of the sensors 102 themselves also can be used to implement at least a portion of the user interface 108. For example, one or more accelerometers or other motion sensors 102 can be used to detect when a person taps the housing of the portable monitoring device 100 with a finger or other object, and then interpret such data as a user input for the purposes of controlling the portable monitoring device 100. For example, double-tapping the housing of the portable monitoring device 100 may be recognized by the processing unit 104 as a user input that will cause a display of the portable monitoring device to turn on from an off state or that will cause the portable monitoring device to transition between different monitoring states, sessions, or modes. For example, in an implementation in which the portable monitoring device includes a single annotation or other general activity-tracking mode, the tapping may cause the processing unit 104 to switch from a state where the portable monitoring device 100 collects and interprets activity data according to rules established for an "active" person to a state where the portable monitoring device collects and interprets activity data according to rules established for a "sleeping" or "resting" person. As another example, tapping the housing of the portable monitoring device 100 may be recognized by the processing unit 104 as a user input that will annotate monitored activity data, such as by, for example, indicating a starting or ending time of an activity session of user-defined duration. In some other implementations, such as in implementations in which the portable monitoring device 100 includes two or more activity-specific activity-tracking modes, the tapping may cause the processing unit 104 to switch from one activity-specific activity-tracking mode to another. For example, tapping may cause the processing unit 104 to switch from a walking mode where the portable monitoring device 100 collects and interprets activity data according to rules established for a "walking" person to a bicycling mode where the portable monitoring device interprets data according to rules established for a bicycle rider.

In some implementations, the processing unit 104 may communicate activity data received from the sensors 102 or retrieved from the memory 106 via the I/O interface 110 to an external or remote computing device (for example, a personal computer, smartphone or multimedia device) or to a back-end server over one or more computer networks. In some implementations, the I/O interface 110 includes a transmitter and a receiver (also referred to collectively herein as a "transceiver" or simply as "transmitting and receiving circuitry") that can transmit the activity data or other information through a wired or wireless connection to one or more external computing devices or to one or more back-end servers (either directly via one or more networks or indirectly via an external computing device that first receives the activity data and subsequently communicates the data via one or more networks to the back-end servers). For example, the memory 106 also can store executable instructions that, when executed by the processing unit 104, cause the processing unit 104 to transmit and receive information via the I/O interface 110. In some implementations, the one or more computer networks include one or more local-area networks (LANs), private networks, social networks, or wide-area networks (WANs) including the Internet. The I/O interface 110 can include wireless communication functionality so that when the portable monitoring device 100 comes within range of a wireless base station or access point, or within range of certain equipped external computing devices (for example, a personal computer, smartphone or multimedia device), certain activity data or other data is automatically synced or uploaded to the external computing device or back-end server for further analysis, processing, viewing, or storing. In various implementations, the wireless communication functionality of I/O interface 110 may be provided or enabled via one or more communications technologies known in the art such as, for example, Wi-Fi, Bluetooth, RFID, Near-Field Communications (NFC), Zigbee, Ant, optical data transmission, among others. Additionally or alternatively, the I/O interface 110 also can include wired-communication capability, such as, for example, a Universal Serial Bus (USB) interface.

In some implementations, one or more back-end servers or computing systems can support a web-based application ("web application"), web site, web page or web portal (hereinafter "web application," "web page," "web site," and "web portal" may be used interchangeably) enabling a user to remotely interact with the portable monitoring device 100, or to interact with or view the activity data or activity metrics calculated based on the activity data, via any computing device (for example, a personal computer, smartphone or multimedia device) capable of supporting a web browser or other web client suitable for use in rendering the web page or web-based application. For example, in some implementations, the data can be stored at an Internet-viewable or Internet-accessible source such as a web site (for example, www.Fitbit.com) permitting the activity data, or data or activity metrics derived or calculated therefrom, to be viewed, for example, using a web browser or network-based application. Hereinafter, reference to a web application, web page, web site or web portal may refer to any structured document or user interface made available for viewing on a client device (for example, a personal computer, smartphone or multimedia device) over any of one or more of the described networks or other suitable networks or communication links.

For example, while the user is wearing a portable monitoring device 100, the processing unit 104 may calculate the user's step count based on activity data received from one or more sensors 102. The processing unit 104 may temporarily store the activity data and calculated step count in the memory 106. The processing unit 104 may then transmit the step count, or raw or pre-processed activity data representative of the user's step count, via I/O interface 110 to an account on a web service (for example, www.fitbit.com), an external computing device such as a personal computer or a mobile phone (especially a smartphone), or to a health station where the data may be stored, further-processed, and visualized by the user or friends of the user.

Other implementations relating to the use of short range wireless communication are described in U.S. patent application Ser. No. 13/785,904, titled "Near Field Communication System, and Method of Operating Same" filed Mar. 5, 2013 which is hereby incorporated herein by reference in its entirety.

In various implementations, the activity metrics that can be tracked, determined, calculate or analyzed by the processing unit 104, or by an external computing device or back-end server based on activity data transmitted from portable monitoring device 100, include one or more of, for example: energy expenditure (for example, calories burned), distance traveled, steps taken, stairs or floors climbed or descended, elevation gained or lost (e.g., based on an altimeter or global positioning satellite (GPS) device), pace, maximum speed, location, direction, heading, ambulatory speed, rotation or distance traveled, swimming stroke count, swimming lap count, swimming distance, bicycle distance, bicycle speed, heart rate, heart rate variability, heart rate recovery, blood pressure, blood glucose, blood oxygen level, skin conduction, skin or body temperature, electromyography data, electroencephalography data, weight, body fat, caloric intake, nutritional intake from food, medication intake, sleep periods, sleep phases, sleep quality, sleep duration, pH levels, hydration levels, and respiration rate. In some implementations, the processing unit 104 also tracks, determines, or calculates metrics related to the environment around the user such as, for example, one or more of: barometric pressure, temperature, humidity, rain/snow conditions, wind speed, other weather conditions, light exposure (ambient light), ultraviolet (UV) light exposure, time or duration spent in darkness, pollen count, air quality, noise exposure, radiation exposure, and magnetic field. Some of the data used to calculate one or more of the metrics just described may be provided to the portable monitoring device from an external source. For example, the user may input his height, weight, or stride in a user profile on a fitness-tracking website and such information may then be communicated to the portable monitoring device 100 via the I/O interface 110 and used to evaluate, in conjunction with activity data measured by the sensors 102, the distance traveled or calories burned by the user.

A general listing of potential types of sensors 102 and activity data types is shown below in Table 1. This listing is not exclusive, and other types of sensors other than those listed may be used. Moreover, the data that is potentially derivable from the listed sensors may also be derived, either in whole or in part, from other sensors. For example, an evaluation of stairs climbed may involve evaluating altimeter data to determine altitude change, clock data to determine how quickly the altitude changed, and accelerometer data to determine whether biometric monitoring device is being worn by a person who is walking (as opposed to standing still).

TABLE 1

| Sensor Type | Activity Data | Potentially-Derivable Activity Data |
| --- | --- | --- |
| Accelerometers | Accelerations experienced at location worn | Rotation, translation, velocity/speed, distance traveled, steps taken, elevation gained, fall indications, calories burned (in combination with data such as user weight, stride, etc.) |
| Gyroscopes | Angular orientation and/or rotation | Rotation, orientation |
| Altimeters | Barometric pressure | Altitude change, flights of stairs climbed, local pressure changes, submersion in liquid |
| Pulse Oximeters | Blood oxygen saturation (SpO2), heart rate, blood volume | Heart rate variability, stress levels, active heart rate, resting heart rate, sleeping heart rate, sedentary heart rate, cardiac arrhythmia, cardiac arrest, pulse transit time, heart rate recovery time, blood volume |
| Galvanic Skin Response Sensors | Electrical conductance of skin | Perspiration, stress levels, exertion/arousal levels |
| Global Positioning System (GPS) | Location, elevation | Distance traveled, velocity/speed |
| Electromyographic Sensors | Electrical pulses | Muscle tension/extension |
| Audio Sensors | Local environmental sound levels | Laugh detection, breathing detection, snoring detection, respiration type (snoring, breathing, labored breathing, gasping), voice detection, typing detection |
| Photo/Light Sensors | Ambient light intensity, ambient light wavelength | Day/night, sleep, UV exposure, TV watching, indoor v. outdoor environment |
| Temperature Sensors | Temperature | Body temperature, ambient environment temperature |
| Strain Gauge Sensors | Weight (the strain gauges may be located in a device remote from the biometric monitoring device, e.g., a Fitbit Aria ™ scale, and communicate weight-related data to the biometric monitoring device, either directly or via a shared account over the Internet) | Body Mass Index (BMI) (in conjunction with user-supplied height and gender information, for example) |
| Bioelectrical Impedance Sensors | Body fat percentage (may be included in remote device, such as Aria ™ scale) | |
| Respiration Rate Sensors | Respiration rate | Sleep apnea detection |
| Blood Pressure Sensors | Systolic blood pressure, diastolic blood pressure | |
| Heart Rate Sensors | Heart rate | |
| Blood Glucose Sensors | Blood glucose levels | |
| Moisture Sensors | Moisture levels | Whether user is swimming, showering, bathing, etc. |

In addition to the above, some biometric data may be calculated or estimated by the portable monitoring device 100 without direct reference to data obtained from the sensors 102. For example, a person's basal metabolic rate, which is a measure of the "default" caloric expenditure that a person experiences throughout the day while at rest (in other words, simply to provide energy for basic bodily functions such as breathing, circulating blood, etc.), may be calculated based on data entered by the user via the user interface 108, or via an application or program (including a web application, mobile application, or client-side software program) executing on an external computing device (for example, a personal computer, smartphone or multimedia device) communicatively coupled with the portable monitoring device 100 via the I/O interface 110 and one or more wired or wireless connections or networks. Such user-entered data may be used, in conjunction with data from an internal clock indicating the time of day, to determine how many calories have been expended by a person thus far in the day to provide energy for basic bodily functions.

As described above, in some example implementations, the portable monitoring device 100, and particularly processing unit 104, includes a default activity-tracking mode also referred to herein as an "annotation" mode. In some such implementations, the activity data monitored while in the default annotation mode can be annotated or otherwise marked to indicate, specify, or delineate the starting and ending time points or other time points of and within an activity session. Again, for purposes of this disclosure, an "activity session" may generally refer to a user-defined duration of time, or a duration of time associated with a particular activity or time of day, in which the device is monitoring activity data. In some implementations, the activity data monitored while in the annotation mode also can be annotated or otherwise marked to indicate, specify, or define a specific activity that is being performed by the user during the activity session such as, for example, walking, running, stair climbing, bicycling, swimming, or even sleeping. In various implementations, the user can annotate the activity data prior to, during, or after completion of an associated activity.

In some implementations, a user can annotate an activity session via physical interactions with the portable monitoring device 100, itself. For example, the user can annotate the activity data using, for example, any of the components described above that may be included within user interface 108. Additionally or alternatively, the user can annotate the activity session via an external or remote computer (for example, a personal computer, a smartphone, or a multimedia device). In some such implementations, one or both of the portable monitoring device 100 and a coupled external computing device also can communicate with one or more back-end servers as described above. In some such implementations, the portable monitoring device or external computing device can transmit the annotations (also referred to herein as "annotation data"), the activity data, as well as information about the portable monitoring device or the user, to the servers for storage and, in some implementations, for additional processing or analysis.

In some such implementations, the portable monitoring device 100, and particular the processing unit 104, is configured to use the sensors 102 to monitor the same type of activity data in the same way regardless of the activity being performed or in which the user in currently engaged. That is, in some implementations, regardless of what activity the user is engaging in, be it walking, running, stair climbing, bicycling, swimming, or even sleeping, the same sensors are used to sense movements or other sensed activity data in the same way. In some implementations in which the processing unit 104 is configured to determine, calculate or analyze one or more activity metrics, the processing unit, itself, can determine which activity metrics to determine, calculate or analyze based on the annotation data received for the activity session.

In some implementations, the portable monitoring device 100 can automatically annotate one or more activity sessions. In some such implementations, the processing unit 104 can analyze the activity data from the sensors 102 dynamically (for example, substantially in real time) and automatically determine a starting point, an ending point, or other time points for which to record timestamps or store markers or digital flags in the memory 106 to annotate the activity data monitored in an activity session. In some other implementations, the processing unit can analyze activity data retrieved from the memory 106 to automatically annotate the stored activity data. In still other implementations, the processing unit 104 can transmit the activity data via I/O interface 110 to one or both of an external computing device (for example, a personal computer, a smartphone or a multimedia device) or a back-end server (either directly over one or more wired or wireless networks or indirectly by way of an external computing device, such as a personal computer, a smartphone or a multimedia device, in conjunction with one or more wired or wireless networks) that then automatically annotates the received activity data. In some of the aforementioned implementations, the annotation data can be stored with the corresponding activity data; that is, together with the activity data in the same locations within the memory 106. In some other implementations, the annotation data can be stored separately from the activity data within the memory 106 but linked to the activity data by way of, for example, one or more tables and timestamps.

In an example implementation, if the portable monitoring device 100 is placed in an annotation mode prior to the wearer going to sleep and then taken out of the annotation mode after the wearer wakes up, e.g., via user interactions or based on sensed biometric or other activity data, the portable monitoring device 100 may record biometric data that indicates that the wearer was largely stationary and horizontal during the time that the biometric monitoring device was in the annotation mode. This, in combination with the time of day that the annotated biometric data was collected, may cause the portable monitoring device to automatically annotate such data as a "sleeping" activity. A wearer of the biometric monitoring device may, alternatively, indicate that the annotated biometric data is associated with a particular activity, e.g., by entering a label or other identifier of the activity in association with the annotated data after the biometric data is exported from the portable monitoring device to a one more back-end servers via a website, web application, mobile application, or other application or by inputting such a label or other identifier into an external computing device (for example, a smartphone, multimedia device, or personal computer) that is paired with the portable monitoring device and within communication range of the portable monitoring device, and particularly the I/O interface 110.

In some other example implementations, the portable monitoring device 100 may automatically detect or determine when the user is attempting to go to sleep, entering sleep, is asleep, or is awoken from a period of sleep. In some such implementations, the portable monitoring device 100 may employ physiological, motion or other sensors to acquire activity data. In some such implementations, the processing unit 104 then correlates a combination of one or more of: motion, heart rate, heart rate variability, respiration rate, galvanic skin response, or skin or body temperature sensing to detect or determine if the user is attempting to go to sleep, entering sleep, is asleep or is awoken from a period of sleep. In response, the portable monitoring device 100 may, for example, acquire physiological data (such as of the type and in the manner as described herein) or determine physiological conditions of the user (such as of the type and in the manner as described herein). For example, a decrease or cessation of user motion combined with a reduction in user heart rate and/or a change in heart rate variability may indicate that the user has fallen asleep. Subsequent changes in heart rate variability and galvanic skin response may be used to determine transitions of the user's sleep state between two or more stages of sleep (for example, into lighter and/or deeper stages of sleep). Motion by the user and/or an elevated heart rate and/or a change in heart rate variability may be used to determine that the user has awoken.

Real-time, windowed, or batch processing to maybe used to determine the transitions between wake, sleep, and sleep stages, as well as in other activity stages. For instance, a decrease in heart rate may be measured in a time window where the heart rate is elevated at the start of the window and reduced in the middle (and/or end) of the window. The awake and sleep stages may be classified by a hidden Markov model using changes in motion signal (e.g., decreasing intensity), heart rate, heart rate variability, skin temperature, galvanic skin response, and/or ambient light levels. The transition points may be determined through a changepoint algorithm (e.g., Bayesian changepoint analysis). The transition between awake and sleep may be determined by observing periods where the user's heart rate decreases over a predetermined time duration by at least a certain threshold but within a predetermined margin of the user's resting heart rate (that is observed as, for instance, the minimum heart rate of the user while sleeping). Similarly, the transition between sleep and awake may be determined by observing an increase in the user's heart rate above a predetermined threshold of the user's resting heart rate.

In some implementations, a back-end server determines which activity metrics to calculate or analyze based on annotation data generated by the server or another server and stored in one or both of the servers, annotation data received from an external computing device, or annotation data also received from the portable monitoring device 100. Additionally, the servers also can determine which activity metrics to calculate or analyze based on an analysis of the tracked activity data. In some such implementations, the portable monitoring device 100 may not track, determine, calculate or analyze any activity metrics at all; rather, the portable monitoring device may monitor the sensed activity data and subsequently store or transmit the activity data for later analysis and processing by an external computing device or back-end servers.

As described above, one or output mechanisms—visual, auditory, or motion/vibration—may be used alone or in any combination with each other or another method of communication to communicate any one of or a plurality of the following information notifications: that a user needs to wake up at certain time (e.g., an alarm); that a user should wake up as they are in a certain sleep phase (e.g., a smart alarm); that a user should go to sleep as it is a certain time; that a user should wake up as they are in a certain sleep phase or stage and in a preselected or previously-user-defined time window bounded by the earliest and latest time that the user wants to wake up; that an email, text or other communication was received; that the user has been inactive for a certain period of time (such a notification function may integrate with other applications like, for instance, a meeting calendar or sleep tracking application to block out, reduce, or adjust the behavior of the inactivity alert); that the user has been active for a certain period of time; that the user has an appointment or calendar event (e.g., a reminder); or that the user has reached a certain activity metric or combination of activity metrics. Also as described above, one or output mechanisms—visual, auditory, or motion/vibration—may be used alone or in any combination with each other or another method of communication to communicate that the user has met or achieved or made progress towards one or more of the following goals: the traversal of a certain distance; the achievement of certain mile (or other lap) pace; the achievement of a certain speed; the achievement of a certain elevation gain; the achievement of a certain number of steps; the achievement of a certain maximum or average heart rate; the completion of a certain number of swimming strokes or laps in a pool.

These examples are provided for illustration and are not intended to limit the scope of information that may be communicated by the device (for example, to the user). As described above, the data used to determine whether or not a goal is achieved or whether the condition for an alert has been met may be acquired from the portable monitoring device 100 or another device. The portable monitoring device 100 itself may determine whether the criteria for an alert, goal, or notification has been met. Alternatively, a computing device in communication with the device (e.g. a server and/or a mobile phone) may determine when the alert should occur. In view of this disclosure, other information that the device may communicate to the user can be envisioned by one of ordinary skill in the art. For example, the device may communicate with the user when a goal has been met. The criteria for meeting this goal may be based on physiological, contextual, and environmental sensors on a first device, and/or other sensor data from one or more secondary devices. The goal may be set by the user or may be set by the device itself and/or another computing device in communication with the device (e.g. a server).

In one example implementation, upon detecting or determining that the user has reached a biometric or activity goal, the portable monitoring device 100 may vibrate to notify the user. For example, the portable monitoring device 100 may detect (or be informed) that the wearer has exceeded a predefined goal or achievement threshold, for example, 10,000 steps taken in one day, and may, responsive to such an event, vibrate to alert or congratulate the user. In some such implementations, if the user then presses a button, the display may turn on and present data about the goal that the user reached, for example, what goal was reached, if the goal was previously reached one or more times on a different day, week, month, or year, or how long it took to reach the goal). In another example, the color and/or intensity of one or more LEDs may serve as notifications that the user is winning or losing against a friend in a competition in, for example, step count. In yet another example, the biometric monitoring device may be a wrist-mounted device that may vibrate or emit audio feedback to notify the user of an incoming email, text message, or other alert. In some such implementations, if the user then moves his or her wrist in a gesture similar to checking a watch, the display of the biometric monitoring device may be turned on and a data display page relating data relevant to the alert may be presented to the user. In yet another example, the biometric monitoring device may present increasingly noticeable feedback methods based on the importance or urgency of the alert. For example, a high priority alert may include audio, vibration, and/or visual feedback, whereas a low priority alert may only include visual feedback. The criteria to distinguish a high priority alert from lower-priority alerts may be defined by the user. For example, a high-priority alert may be triggered if an email message or text is sent with a particular priority, e.g., "urgent," if an email message or text is sent from a particular person, e.g., a person that the user has identified as being high-priority, if a meeting notification or reminder is received or occurs, if a certain goal is achieved or if a dangerous health condition, such as a high heart rate is detected.

As described above, in some other implementations, the portable monitoring device 100 may operate within or according to a plurality of modes. For example, various modes may include: a general or default activity-tracking mode such as the annotation mode described above, a timer mode, a stopwatch mode, a clock/time/watch mode, a sleep-monitoring (or "sleep-tracking") mode, a work mode, a home mode, a commute mode, as well as one or more activity-specific activity-tracking modes for tracking user activities such as biking, swimming, walking, running, stair-climbing, rock climbing, weight-lifting, treadmill exercise, and elliptical machine exercise. In some multi-mode implementations, the portable monitoring device 100 also enables a user to annotate activity data monitored in one or more modes including one or more activity-specific activity-tracking modes as described above.

The processing unit 104 may automatically determine or select a mode for the device to operate in based on a plurality of signals, data or other information. For example, the processing unit may automatically select a mode based on one or more activity metrics (for example, a step count, stair or floor count, or a number of calories burned) or, additionally or alternatively, based on one or more of: contextual or environmental data (for example, time of day, GPS or other determined or entered location or position data, ambient light brightness, temperature, or humidity); physiological or other person-centric data (for example, heart rate, body temperature, hydration level, or blood oxygen level); or system condition data (for example, in response to a low battery or low memory); or based on one or more user-defined conditions being met.

In some implementations, the portable monitoring device itself can determine which activity data to monitor, or, additionally or alternatively, which activity (or sleep) metrics (hereinafter "sleep metrics" also may generally be referred to as "activity metrics") to determine, calculate or analyze, based on which of the activity-tracking or other modes is currently active or initiated. Additionally or alternatively, in some implementations, one or both of an external computing device or a back-end server can request certain activity data from the portable monitoring device based on which of the activity-tracking modes is currently active or initiated. Additionally or alternatively, in some implementations, one or both of an external computing device or a back-end server can receive all activity data monitored by the portable monitoring device and subsequently filter or otherwise selectively process certain activity data to determine, calculate or analyze certain activity metrics based on which of the activity-tracking modes is currently active or initiated.

In some multi-mode implementations, a user can select which of the modes is currently active or initiated via the user interface 108, or via an application or program (including a web application, mobile application, or client-side software program) executing on an external computing device (for example, a personal computer, smartphone or multimedia device) communicatively coupled with the portable monitoring device 100 via the I/O interface 110 and one or more wired or wireless connections or networks. For example, a user may select the mode of the portable monitoring device 100 using an application on a smartphone that sends the mode selection to a server. The server, in turn, sends the mode selection to an external computing device that then sends the mode selection to the portable monitoring device 100 via the I/O interface 110. Alternatively, the smart phone application (or the server) may send the mode selection directly to the portable monitoring device 100.

In some implementations, a user also can select which activity metrics to track while in each of the corresponding activity-tracking modes. As described above, in some implementations, the portable monitoring device 100 also can be configured to automatically switch among two or more activity-tracking or other modes. In some such implementations, the processing unit 104 can analyze the activity data from the sensors 102 and automatically determine a most suitable, appropriate, or optimal activity-tracking or other mode to switch into based on the analysis of the activity data dynamically in substantially real-time. In some other such implementations, the processing unit 104 can transmit the activity data via I/O interface 110 through a wired or wireless connection to one or both of an external computing device or back-end server that then analyzes the activity data, determines the most suitable, appropriate, or optimal activity-tracking or other mode to switch into, and subsequently transmits one or more instructions to the portable monitoring device 100 that, when executed by the processing unit 104, cause the processing unit 104 (in conjunction with one or more other components described above) to switch into the determined mode.

In some implementations, the portable monitoring device 100 includes an alarm clock function intended to wake the wearer or user from sleep or otherwise alert the user. In some such implementations, the portable monitoring device 100 acts as a wrist-mounted vibrating alarm to silently wake the user from sleep. The portable monitoring device also can be configured to track the user's sleep quality, waking periods, sleep latency, sleep efficiency, sleep stages (e.g., deep sleep vs REM), or other sleep-related metrics through one or a combination of heart rate, heart rate variability, galvanic skin response, motion sensing (e.g., accelerometer, gyroscope, magnetometer), and skin temperature. In some implementations, the user may specify a desired alarm time or window of time (e.g. set alarm to go off between 7 and 8 am). In some such implementations, the processing unit 104 uses one or more of the sleep metrics to determine an optimal time within the alarm window to wake the user. In some implementations, when the vibrating alarm is active, the user may cause it to hibernate, snooze, or turn off by slapping or tapping the device (which is detected, for example, via motion sensor(s), a pressure/force sensor and/or capacitive touch sensor in the device). In one specific implementation, the portable monitoring device 100 can be configured to attempt to arouse the user at an optimum point in the sleep cycle by starting a small vibration at a specific user sleep stage or time prior to the alarm setting. It may progressively increase the intensity or noticeability of the vibration as the user progresses toward wakefulness or toward the alarm setting. Similar to the way a conventional alarm clock functions, the wearer or user may have the ability to set one or more daily, periodic, or other recurring alarms. Additionally, the alarm function can be configured to "snooze," i.e., temporarily stop the alarm for a short period of time, typically minutes, and then have the alarm re-trigger.

As a result of the small size of many portable monitoring devices, many such monitoring devices have limited space to accommodate various user interface components. For example, Fitbit manufactures a variety of extremely compact portable monitoring devices, including biometric tracking units, that each incorporate a suite of sensors, a battery, a display, a power-charging interface, and one or more wireless communications interfaces. In some such examples, the portable monitoring devices also incorporate a vibramotor and/or a button. These components may be housed, for example, within housings measuring approximately 2" long, 0.75" wide, and 0.5" thick (Fitbit Ultra™); approximately 1.9" in length, 0.75" wide, and 0.375" thick (Fitbit One™); approximately 1.4" long, 1.1" wide, and 0.375" thick (Fitbit Zip™); and approximately 1.3" in length, 0.5" wide, and 0.25" thick (Fitbit Flex™). Of course, housings of other sizes may be used in other implementations of biometric monitoring devices; the above list is merely intended to illustrate the small size of many such biometric monitoring devices.

Despite the small sizes of the above-listed Fitbit devices, each includes a display of some type—the Fitbit Ultra, Fitbit One, and Fitbit Zip, for example, all include small pixelated display screens capable of outputting text, numbers, and graphics. The Fitbit Flex, due to its smaller size, uses discrete light-emitting diode (LED) indicators, e.g., 5 LEDs arranged in a row, to convey information visually. Each of the above-listed Fitbit devices also have an input mechanism that allows a user to affect some aspect of the device's operation. For example, the Fitbit Ultra and Fitbit One each include a discrete pushbutton that allows a user to affect how the device operates. The Fitbit Zip and Fitbit Flex, by contrast, do not have a discrete pushbutton but are instead each configured to detect, using their biometric sensors, when the user taps the housing of the device; such events are construed by the processor or processors of such devices as signaling a user input, i.e., acting as the input mechanism.

One component of the portable monitoring device 100 that may be limited in size or performance is the power source 114, for example, a rechargeable, removable, or replaceable battery, capacitor, etc. In some implementations, the portable monitoring device 100 can be configured to remain in an "always on" state to allow it to continually collect activity data throughout the day and night. Given that the sensors 102 and processing unit 104 of the portable monitoring device must generally remain powered to some degree in order to collect the activity data, it can be advantageous to implement power-saving features elsewhere in the device, such as by, for example, causing a display to automatically turn off after a period of time. The Fitbit Ultra™ is an example of a portable monitoring device that includes a data display that is typically turned off to save power unless the device is being interacted with by the user. A typical user interaction may be provided by, for example, pressing a button on the device.

In some implementations, a housing of the portable monitoring device 100 itself is designed or configured such that it may be inserted into, and removed from, a plurality of compatible cases, housings, or holders (hereinafter "cases," "housings," and "holders" may be used interchangeably). For example, in some implementations, the portable monitoring device 100 is configured for removable insertion into a wristband or armband that can be worn on a person's wrist, forearm or upper arm. In some implementations, the portable monitoring device is additionally or alternatively configured for removable insertion into a belt-clip case or configured for coupling with a clip that can be attached to a person's belt or clothing. As used herein, the term "wristband" may refer to a band that is designed to fully or partially encircle a person's forearm near the wrist joint. The band can be continuous, for example, without any "breaks"; that is, it may stretch to fit over a person's hand or have an expanding portion similar to a dress watchband. Alternatively, the band can be discontinuous, for example, having a clasp or other connection enabling a user to close the band similar to a watchband. In still other implementations, the band can simply be simply "open," for example, having a C-shape that clasps the wearer's wrist. Hereinafter, a portable monitoring device that is inserted, combined, or otherwise coupled with a separate removable case or some other structure enabling it to be worn or easily carried by or attached to a person or his clothing may be referred to as a "portable monitoring system."

Figure 2:
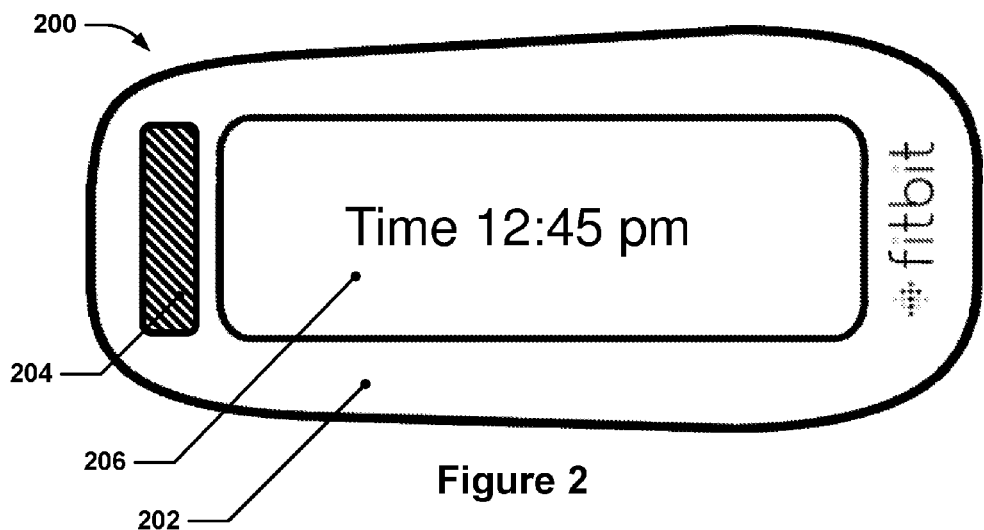
FIG. 2 depicts a portable monitoring device that may be inserted into a holder with a belt clip or into a pocket on a wristband.
Figure 3:
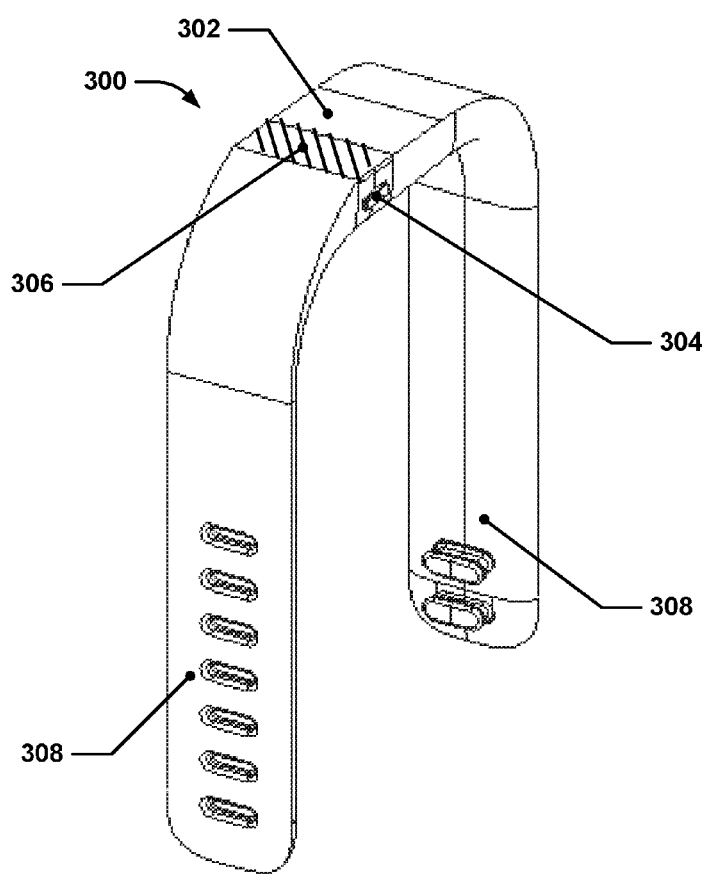
FIG. 3 depicts a portable monitoring device that may be worn on a person's forearm like a wristwatch.
Figure 4:
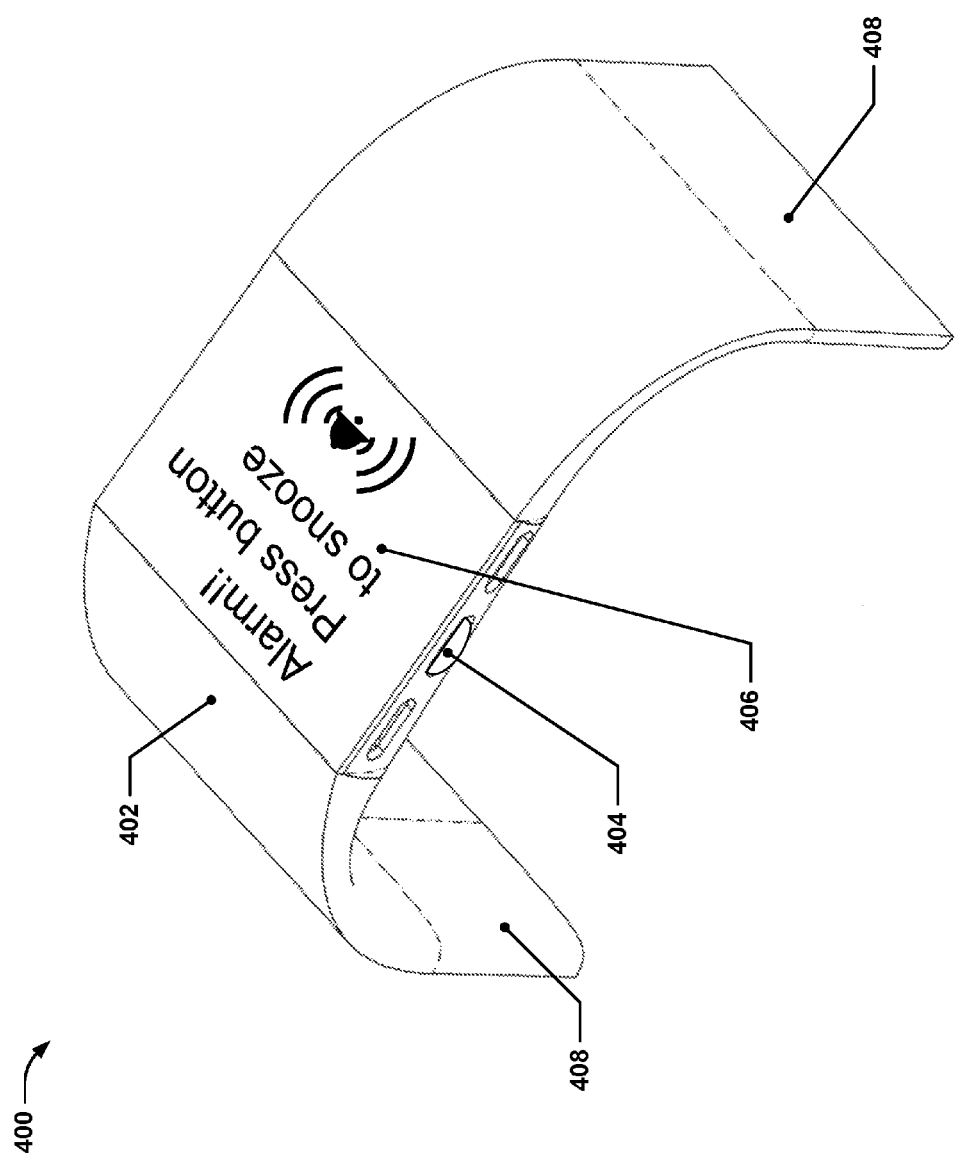
FIG. 4 depicts another example of a portable monitoring device that may be worn on a person's forearm.

As mentioned above, various implementations of portable monitoring devices described herein may have shapes and sizes adapted for coupling to the body or clothing of a user (e.g., secured to, worn, borne by, etc.). Various examples of such portable monitoring devices are shown in FIGS. 2, 3, and 4. FIG. 2 depicts a monitoring device similar in shape to a Fitbit One, which may be inserted into a holder with a belt clip or into a pocket on a wristband. Portable monitoring device 200 has a housing 202 that contains the electronics associated with the biometric monitoring device 200. A button 204 and a display 206 may be accessible/visible through the housing 202. FIG. 3 depicts a portable monitoring device that may be worn on a person's forearm like a wristwatch, much like a Fitbit Flex. Portable monitoring device 300 has a housing 302 that contains the electronics associated with the biometric monitoring device 300. A button 304 and a display 306 may be accessible/visible through the housing 302. A wristband 308 may be integrated with the housing 302. FIG. 4 depicts another example of a portable monitoring device that may be worn on a person's forearm like a wristwatch, although with a bigger display than the portable monitoring device of FIG. 3. Portable monitoring device 400 has a housing 402 that contains the electronics associated with the portable monitoring device 400. A button 404 and a display 406 may be accessible/visible through the housing 402. A wristband 408 may be integrated with the housing 402.

Further embodiments and implementations of portable monitoring devices can be found in U.S. patent application Ser. No. 13/156,304, titled "Portable Biometric Monitoring Devices and Methods of Operating Same" filed Jun. 8, 2011 which is hereby incorporated by reference in its entirety.

Unless the context (where the term "context" is used per its typical, general definition) of this disclosure clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also generally include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list, and any combination of the items in the list. The term "implementation" refers to implementations of techniques and methods described herein, as well as to physical objects that embody the structures and/or incorporate the techniques and/or methods described herein.

There are many concepts and implementations described and illustrated herein. While certain features, attributes and advantages of the implementations discussed herein have been described and illustrated, many others, as well as different and/or similar implementations, features, attributes and advantages, are apparent from the description and illustrations. As such, the above implementations are merely exemplary and are not intended to be exhaustive or to limit the disclosure to the precise forms, techniques, materials and/or configurations disclosed. Many modifications and variations are possible in light of this disclosure. Other implementations may be utilized and operational changes may be made without departing from the scope of the present disclosure. As such, the scope of the disclosure is not limited solely to the description above because the description of the above implementations has been presented for the purposes of illustration and description.

Importantly, the present disclosure is neither limited to any single aspect nor implementation, nor to any single combination and/or permutation of such aspects and/or implementations. Moreover, each of the aspects of the present disclosure, and/or implementations thereof, may be employed alone or in combination with one or more of the other aspects and/or implementations thereof. For the sake of brevity, many of those permutations and combinations will not be discussed and/or illustrated separately herein.

What is claimed is:

1. A device comprising:
    at least one motion sensor to sense motion of the device and to provide activity data based on the sensed motion;
    at least one processor to:
        receive the activity data;
        receive or generate annotation data to annotate the activity data with one or more markers or indicators to define one or more characteristics of a physical activity session, the one or more markers or indicators defining a first time duration of the physical activity session;
        determine a value of a first activity metric using the activity data received during the first time duration, the first activity metric value defining at least one of the one or more characteristics of the physical activity session; and
        determine a value of a second activity metric using the activity data received during the first time duration and activity data received during a second time duration different than the first time duration, the second activity metric value defining a characteristic of a period of time that covers the first time duration and the second time duration;
    at least one feedback device to provide an indication to a user based on the first activity metric value; and
    a portable housing that encloses at least portions of the at least one motion sensor, the at least one processor and the at least one feedback device.

2. The device of claim 1, wherein the one or more markers or indicators further define a type of activity performed during the physical activity session.

3. The device of claim 1, wherein a type of the first activity metric is the same as a type of the second activity metric.

4. The device of claim 3, wherein the first activity metric value includes a number of steps taken during only the first time duration, and wherein the second activity metric value includes a number of steps taken during both the first time duration and the second time duration.

5. The device of claim 1, wherein a type of the first activity metric is different than a type of the second activity metric.

6. The device of claim 1, wherein the at least one feedback device includes a display, wherein the at least one processor is configured to cause the display to display an indication associated with the first activity metric value.

7. The device of claim 1, wherein the at least one feedback device includes at least one vibrating device, wherein the at least one processor is configured to cause the at least one vibrating device to provide a haptic indication associated with the first activity metric value.

8. The device of claim 1, wherein the at least one processor is configured to determine which activity data to track based on the one or more markers or indicators.

9. The device of claim 1, wherein the at least one processor is configured to select a type of the first activity metric to determine based on the one or more markers or indicators.

10. The device of claim 1, wherein the first activity metric value is a distance traveled, a number of steps taken, a number of stairs or floors climbed, an elevation change, a number of calories burned, a pace, a maximum speed, a stroke count, a lap count, a blood pressure, or a heart rate.

11. The device of claim 1, wherein the at least one processor is configured to analyze the activity data and to generate the one or more markers or indicators based on the analysis of the activity data.

12. The device of claim 1, wherein the at least one processor is configured to generate the one or more markers or indicators based on a device state or mode.

13. The device of claim 1, wherein the at least one processor is configured to determine that an annotation mode is active, and wherein the at least one feedback device provides the indication to the user based further on the determination that the annotation mode is active.

14. The device of claim 1, wherein the at least one processor is configured to switch among a plurality of activity-tracking modes based on the one or more markers or indicators, and wherein the at least one processor is configured to select a type of the first activity metric to determine based on which of the plurality of activity-tracking modes is currently active.

15. The device of claim 14, wherein the plurality of activity-tracking modes includes at least one of a running mode, a walking mode, a stair-climbing mode, a bicycling mode, a swimming mode, or a sleep-tracking mode.

16. The device of claim 1, wherein:
    the device further includes at least one user input device included in or integrated with the housing for receiving or sensing user input;
    the at least one processor is further configured to receive and interpret the user input received or sensed via the at least one user input device; and
    the at least one processor is configured to receive user input via the at least one user input device and to define the one or more markers or indicators based on the user input.

17. The device of claim 16, wherein the at least one processor is configured to define a start time of the physical activity session, an end time of the physical activity session, the first time duration of the physical activity session, or a type of activity performed during the physical activity session based on the user input.

18. The device of claim 1, wherein:
    the device further includes transmitting and receiving circuitry;
    the transmitting and receiving circuitry is configured for wireless communication over a network; and
    the at least one processor is configured to receive and interpret user input received by the receiving circuitry.

19. The device of claim 1, wherein the at least one processor is configured to cause the at least one feedback device to indicate to a user that a goal or a progress point en route to a goal has been met based on the first activity metric value.

20. The device of claim 1, further including at least one of: a gyroscope, a physiological sensor, a biometric sensor, an altitude sensor, a temperature sensor, a light sensor, or a heart-rate sensor; and wherein the at least one processor is configured to determine the first activity metric value further based on data from at least one of: the gyroscope, the physiological sensor, the biometric sensor, the altitude sensor, the temperature sensor, the light sensor, or the heart-rate sensor.

21. A method implemented by a portable monitoring device, comprising:
sensing, by at least one motion sensor, motion of the portable monitoring device and providing activity data based on the sensed motion;
receiving, by at least one processor, the activity data;
receiving or generating, by the at least one processor, annotation data to annotate the activity data with one or more markers or indicators;
using the one or more markers or indicators, delineating, within the activity data, a starting point of a physical activity session;
determining, by the at least one processor, a value of a first activity metric using the activity data received after the starting point of the physical activity session;
determining, by the at least one processor, a value of a second activity metric using the activity data received before and after the starting point of the physical activity session; and
providing an indication to a user based on the first activity metric value or the second activity metric value based on whether an annotation mode is active.

22. The method of claim 21, wherein the one or more markers or indicators further define a type of activity performed during the physical activity session.

23. The method of claim 21, wherein a type of the first activity metric is the same as a type of the second activity metric.

24. The method of claim 21, wherein the at least one processor is configured to determine which activity data to track based on the one or more markers or indicators.

25. The method of claim 21, further including selecting, by the at least one processor, a type of the first activity metric to determine based on the one or more markers or indicators.

26. The method of claim 21, wherein the first activity metric value is a distance traveled, a number of steps taken, a number of stairs or floors climbed, an elevation change, a number of calories burned, a pace, a maximum speed, a stroke count, a lap count, a blood pressure, or a heart rate.

27. The method of claim 21, further including analyzing, by the at least one processor, the activity data and generating, by the at least one processor, the one or more markers or indicators based on the analysis of the activity data.

28. The method of claim 21, wherein the at least one processor is configured to generate the one or more markers or indicators based on a device state or mode.

29. The method of claim 21, further including:
switching, by the at least one processor, among a plurality of activity-tracking modes based on the one or more markers or indicators; and
selecting, by the at least one processor, a type of the first activity metric to determine based on which of the plurality of activity-tracking modes is currently active.

30. The method of claim 21, further including determining, by the at least one processor, the first activity metric value further based on data from at least one of: a gyroscope, a physiological sensor, a biometric sensor, an altitude sensor, a temperature sensor, a light sensor, or a heart-rate sensor.

* * * * *